(12) United States Patent
Leese

(10) Patent No.: US 8,343,912 B2
(45) Date of Patent: Jan. 1, 2013

(54) ANTIBIOTIC COMPOSITIONS FOR THE TREATMENT OF GRAM NEGATIVE INFECTIONS

(75) Inventor: Richard A. Leese, Suffern, NY (US)

(73) Assignee: Biosource Pharm, Inc., Spring Valley, NY (US)

( * ) Notice: Subject to any disclaimer, the term of this patent is extended or adjusted under 35 U.S.C. 154(b) by 283 days.

(21) Appl. No.: 12/644,943

(22) Filed: Dec. 22, 2009

(65) Prior Publication Data

US 2010/0160215 A1    Jun. 24, 2010

Related U.S. Application Data

(60) Provisional application No. 61/140,408, filed on Dec. 23, 2008.

(51) Int. Cl.
*A61K 38/12* (2006.01)
*C07K 7/62* (2006.01)

(52) U.S. Cl. .......... 514/2.8; 514/2.9; 514/21.1; 530/319

(58) Field of Classification Search ................ None
See application file for complete search history.

(56) References Cited

U.S. PATENT DOCUMENTS

| | | | |
|---|---|---|---|
| 3,753,970 A | 8/1973 | Bouchaudon et al. | |
| 3,854,480 A | 12/1974 | Zaffaroni | |
| 4,091,092 A | 5/1978 | Parker et al. | |
| 4,399,067 A | 8/1983 | Debono et al. | |
| 4,452,775 A | 6/1984 | Kent | |
| 4,482,487 A | 11/1984 | Abbott et al. | |
| 4,524,135 A | 6/1985 | Abbott et al. | |
| 4,537,717 A | 8/1985 | Abbott et al. | |
| RE32,310 E | 12/1986 | Debono | |
| RE32,311 E | 12/1986 | Debono | |
| 5,028,590 A | 7/1991 | Fukuda et al. | |
| 5,039,789 A | 8/1991 | Fukuda et al. | |
| 5,041,567 A | 8/1991 | Rogers et al. | |
| 5,239,660 A | 8/1993 | Ooi | |
| 6,380,356 B1 | 4/2002 | Griffin et al. | |
| 6,511,962 B1 | 1/2003 | Borders et al. | |
| 2001/0021697 A1* | 9/2001 | Lowenstein et al. | 514/12 |
| 2003/0224475 A1 | 12/2003 | Leese et al. | |
| 2008/0207874 A1 | 8/2008 | Leese et al. | |
| 2008/0279820 A1* | 11/2008 | Hicks et al. | 424/85.6 |

FOREIGN PATENT DOCUMENTS

| | | |
|---|---|---|
| JP | 2003-505042 | 2/2003 |
| WO | WO 95/05384 | 2/1995 |
| WO | WO 01/05815 A1 | 1/2001 |
| WO | WO 01/44271 | 6/2001 |
| WO | WO 01/44272 | 6/2001 |
| WO | WO 01/44274 | 6/2001 |
| WO | WO 02/05837 A1 | 1/2002 |
| WO | WO 02/055543 A2 | 7/2002 |
| WO | WO 03/014147 | 2/2003 |
| WO | WO 2006/083317 A2 | 8/2006 |
| WO | WO 2010/075416 A1 | 7/2010 |

OTHER PUBLICATIONS

Barnett, M. et al. "Sodium Sulphomethyl Derivatives of Polymyxins" *Br. J. Pharmacol.* 23:552-574 (1964).
Barrett, et al. "Edman Stepwise degradation of polypeptides: a new strategy employing mild basic cleavage conditions" *Tetrahedron Letters* 26(36):4375-4378 (1985).
Berendsen, H., J., "A Glimpse of the Holy Grail?", *Science*, 282: 642-643 (Oct. 1998).
Berge, et al. "Pharmaceutical Salts" *J. Pharm. Sci.* 66(1):1-19 (1977).
Boeck, et al. "Deacylation of A21978C, an acidic Lipopeptide Antibiotic Complex, by *Actinoplanes utahensis*" *J. Antibiot.* 41(8): 1085-1092 (1988).
Boeck, et al. "Deacylation of Echinocandin B by *Actinoplanes utahensis*" *J. Antibiot.* 42(3):382-388 (1989).
Bradley, C., et al., "Limits of Cooperativity in a Structurally Modular Protein: Response of the Notch Ankyrin Domain to Analogous Alanine Substitutions in Each Repeat", *J. Mol. Biol.*, 324: 373-386 (2002).

(Continued)

*Primary Examiner* — Jeffrey E Russel
(74) *Attorney, Agent, or Firm* — Hamilton, Brook, Smith & Reynolds, P.C.

(57) ABSTRACT

Provided herein is an antibacterial compound of the following formula:

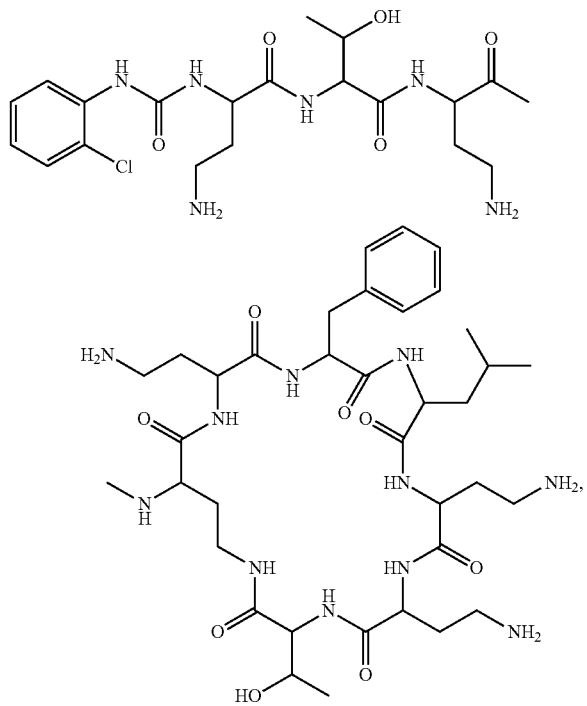

or a pharmaceutically acceptable salt thereof. The antibacterial compound has antibacterial properties against a diverse range of gram negative bacteria and reduced toxicity compared to polymyxins such as polymyxin B. Also provided are antibacterial pharmaceutical compositions containing the antibacterial compound, as well as methods for preparing the antibacterial compound.

15 Claims, 2 Drawing Sheets

OTHER PUBLICATIONS

Brandt, et al. "Abnormal behaviour of proline in the isothiocyanate degradation" *Physiol. Chem.*, 357:1505-1508 (1976).

Brownlee, G., et al., "Remarks on Clinical Results with Polymyxin A and B", *Annals New York Academy of Sciences*, 51(5): 998-1000 (Jun. 1949).

Brownlee, G., et al., "Comparative Biological Studies of Polymyxin A and Polymixin D", *Annals New York Academy of Sciences*, 51(5): 891-896 (Jun. 1949).

Bryer, M., et al, "Pharmacology of Polymyxin", *Annals New York Academy of Sciences*, 51(5): 935-943 (Jun. 1949).

Brownlee, G., et al., "The Pharmacology of Polymyxin A, B, and D", *Annals New York Academy of Sciences*, 51(5): 952-967 (Jun. 1949).

Bruch, M., et al., "Higher-Order Structure of Polymyxin B: The Functional Significance of Topological Flexibility", *J. Am.Chem. Soc.* 121: 11993-12001 (1999).

Catch, J.R., et al.. "The Chemistry of Polymyxin A", *The Wellcome Chemical Research Laboratories*, 51(5): 917-923 (Jun. 1949).

Chihara, et al. "Chemical Synthesis and Characterization of α-N-Octanoyl and Other α-N-Acyl Colistin Nonapeptide Derivatives" *Agr. Biol. Chem.*, 37(12): 2709-2717 (1973).

Chihara, et al. "Chemical Synthesis and Characterization of *n*-Fattyacyl Mono-Aminoacyl Derivatives of Colistin Nonapeptide" *Agr. Biol. Chem.*, 38(10): 1767-1777 (1974).

Chihara, et al. "Chemical synthesis, isolation, and characterization of α-N-fattyacyl colistin nonapeptide with special reference to the correlation between antimicrobial activity and carbon number offattyacyl moiety" *Agr. Biol. Chem.*, 38(3): 521-529 (1974).

Choi, et al., "Identification of a Polymyxin Synthetase Gene Cluster of *Paenibacillus polymyxa* and Heterologous Expression of the Gene in *Bacillus subtillis*", *Journal of Bacteriology*, 191(10): 3350-3358 (May 2009).

Clausell, A. et al. "Membrane Association and Contact Formation by a SynthetiC Analogue of Polymyxin B and Its Fluorescent Derivatives" *J. Phys. Chem. B* 110:44654471 (2006).

Clausell, A. et al. "Synthesis and Membrane Action of Polymyxin B Analogues" *Luminescence* 20: 117-123 (2005).

"Designing Custom Peptides," from SIGMA Genosys, pp. 1-2; http://www.sigma-genosys.com/peptide_design.asp, retrieved from the internet on Dec. 16, 2004.

De Visser, et al. "Solid-phase synthesis of polymyxin B1 and analogues via a safety-catch approach" *J. Pept. Res.*, 61:298-306 (2003).

Duwe, et al. "In Vitro Cytotoxicity and Antibiotic Activity of Polymyxin B Nonapeptide" *Antimicrob. Agents Chemotherapy*, 30:340-341 (1986).

Elverdam, et al. "Isolation and Characterization of Three New Polymyxins in Polymyxins B and E by High-Performance Liquid Chromatography" *J. Chromatography*, 218: 653-661 (1981).

Evans, et al. "Polymyxin B Sulfate and Colistin: Old Antibiotics for Emerging Multiresistant Gram-Negative Bacteria" *Annals of Pharmacotherapy*, 33:960-967 (1999).

Extended European Search Report for EP Application No. 10184953.7 dated Apr. 6, 2011.

Falagas, et al. "Colistin: The Revival of Polymyxins for the Management of Multidrug-Resistant Gram-Negative Bacterial Infections" *Rev. Anti-Infect. Agents*. 40: 1333-1341 (2005); Erratum *Rev. Anti-Infect. Agents* 42: 1819 (2006).

Fostel, et al. "Emerging novel antifungal agent" *Drug Discovery Today* 5:25-32 (2000).

Frecer, V. et al. "De Novo Design of Potent Antimicrobial Peptides" *Antimicrob. Agents Chemother*. 48(9):3349-3357 (2004).

Gershonov, et al. "A Novel Approach for a Water-Soluble Long-Acting Insulin ProDrug: Design, Preparation, and Analysis of [(2-Sulfo)-9-Fluorenylmethoxycarbonylh-Insulin" *J. Med. Chem.* 43(13):2530-2537 (2000).

Han, et al. "Current developments in stepwise Edman degradation of peptides and proteins" *Int. J. Biochem.* 17(4):429-445 (1985).

Han, et al. "Dégradation récurrente d'EDMAN" *Biochimie* 59:557-576 (1977).

Hausmann, et al. "Polymyxin B1. Fractionation, molecular weight determination, amino acid and fatty acid composition" *J. Am. Chem. Soc.* 76:4892-4896 (1954).

International Preliminary Report on Patentability for International Application No. PCT/US2005/023343 dated Jan. 9, 2007.

Jarolmen, et al. "Activity of Minocycline Against R-Factor Carrying *Enterobacteriaceae*" *Infect. Immun.* 1(4):321-326 (1970).

Kanazawa, K. et al. "Contribution of Each Amino Acid Residue in Polymyxin B3 to Antimicrobial and Lipopolysaccharide Binding Activity" *Chem. Pharm. Bull.* 57(3):240-244 (2009).

Kato, et al. "The Structure of Octapeptin D (Studies on Antibiotics from the Genus *Bacillus*. XXVIII)" *J. Antibiotics* 33(2): 186-191 (Feb. 1980).

Katsuma, N. et al. "Development of Des-Fatty Acyl-Polymyxin B Decapeptide Analogs with *Pseudomonal aeruginosa-Specific* Antimicrobial Activity" *Chem. Pharm. Bull.* 57(4):332-336 (2009).

Kimura, et al. "Polymyxin acylase: purification and characterization, with special reference to broad substrate specificity" *Agric. Biol. Chem.*, 53(2):497-504 (1989).

Kimura, et al. "Polymyxin B Octapeptide and Polymyxin B Heptapeptide are Potent Outer Membrane Permeability-Increasing Agents" *J. Antibiot.*, 45:742-749 (1992).

Kimura, et al. "Polymyxin P, New Antibiotics of Polymyxin Group" *J. Antibiot.*, XXII(9): 449-450 (Sep. 1969).

Kleinkauf, H. et al. "Nonribosomal biosynthesis of peptide antibiotics" *Eur. J. Biochem.*, 192:1-15 (1990).

Kline, et al. "Synthesis and characterization of the colistin peptide polymyxin E1 and related antimicrobial peptides" *J. Peptide Res.*, 57(3):175-187 (2001).

Kreuzman, et al. "Membrane-associated echinocandin B deacylase of *Actinoplanes utahensis*: purification, characterization, heterologous cloning and enzymatic deacylation reaction" *J. Ind. Microbial. Biotechnol.* 24:173-180 (2000).

Kristensen, H.K. et al. "Separation of Polymyxins by Micellar Electrokinetic Capillary Chromatography" *J. Chromatography* 628:309-315 (1993).

Kurihara, et al. "Studies on the compounds related to colistin. V. Synthesis and pharmacological activity of colistin analogues" *Yakugaku Zasshi*, 92: 129-134 (1972).

Li, C. et al. "Incremental Conversion of Outer-Membrane Permeabilizers into Potent Antibiotics for Gram-Negative Bacteria" *J. Am. Chem. Soc.* 121:931-940 (1999).

Liu et al. "A novel fmoc-based anchorage for the synthesis of protected peptide on solid phase" *Int. J. Pept. Protein Res*. 35:95-98 (1990).

Mares, J., et al., "Interactions of Lipopolysaccharide and Polymyxin Studied by NMR Spectroscopy", *J. Biol. Chem.*, 284(17): 11498-11506 (Apr. 24, 2009).

Markou, et al. "Intravenous colistin in the treatment of sepsis from multiresistant Gramnegative bacilli in critically ill patients" *Critical Care*, 7:R78-R83 (2003).

Martin, et al. "Isolation, structural characterization, and properties of mattacin (polymyxin M), a cyclic peptide antibiotic produced by *Paenibacillus kobensis* M" *J. Bioi. Chem.*, 278(15):13124-13132 (2003).

Matsenaga, H., et al., "Polymyxcin P, Antibiotics from *Bacillus polymyxa* T-39; Fermentation, Isolation, Structure Elucidation and Antibacterial Activity", *Mukogawa Women's University* Nishimoyia 663, 37: 37-43 (1995).

McCallister, et al. "Antimicrobial properties of liposomal polymyxin B" *J. Antimicrob. Chemother.*, 43:203-210 (1999).

Merrifield, et al. "9-(2-sulfo)fluorenylmethyloxycarbonyl chloride, a new reagent for the purification of synthetic peptides" *J. Org. Chem.*, 43(25):4808-4816 (1978).

Notification Concerning Transmittal of International Preliminary Report on Patentability for International Patent Application No. PCT/US2009/069247 dated Jul. 7, 2011.

Molina, J. et al. "New Information about the Polymyxin/Colistin Class of Antibiotics" *Expert Opin. Pharmacother*. 10(17):2811-2828 (2009).

Mutter et al. "A New Base-Labile Anchoring Group for Polymer-Supported Peptide Synthesis" *Helv. Chico. Acta*. 67:2009 (1984).

Nakajima "Structure-activity relationship of colistins" *Chem. Pharm. Bull.*, 15(8): 1219-1224 (1967).

Ngo, J., et al., "Computational Complexity, Protein Structure Prediction, and the Levinthal Paradox", *The Protein Folding Problem and Tertiary Structure Prediction*, pp. 491-495, (1994).

Notification of Transmittal of International Search Report and the Written Opinion of the International Searching Authority, or the Declaration of International Application No. PCT/US2005/023343 dated Dec. 6, 2006.

O'Dowd, H. et al. "Preparation of Tetra-Boc-Protected Polymyxin B Nonapeptide" *Tetrahedron Lett.* 48:2003-2005 (2007).

Ohki, K., et al., "Synthesis and Antimicrobial Activit6y of Polymyxin B Component Peptides",*Peptide Science*, p. 189-192 (2002).

Okimura, K. et al. "Chemical Conversion of Natural Polymyxin B and Colistin to Their *N*-Terminal Derivatives" *Bull. Chemn. Soc.* Jpn. 80(3):543-552 (2007).

Okimura, K. et al. "Semi-synthesis of Polymyxin B (2-10) and Colistin (2-10) Analogs Employing the Trichloroethoxycarbonyl (Troc) Group for Side Chain Protection of a, *y*-Diaminobutyric Acid Residues" *Chem. Pharm. Bull.* 55(12):1724-1730 (2007).

Orwa, J.A. et al. "Isolation and Structural Characterization of Colistin Components" *J. Antibiotics* 54(7):595-599 (2001).

Orwa, J.A. et al. "Isolation and Structural Characterization of Polymyxin B Components" *J. Chromatography A* 912:369-373 (2001).

Parker, et al. "EM49: A New Peptide Antibiotic II. Chemical Characterization" *J. Antibiot.*, 26(8):449-456 (1975).

Parker, et al. "EM49: A New Peptide Antibiotic IV. The Structure of EM49" *J. Antibiot.*, 28(5):379-389 (1975).

Pristovsek, P, et al., "Solution Structure of Polymyxins B and E and Effect of Binding to Lipopolysaccharide: An NMR and Molecular Modeling Study", *J. Med. Chem.* 42: 4604-4613 (1999).

Puar, M.S. "Carbon-13 NMR Studies of EM49 and Related Octapeptins" *J. Antibiotics* 33:760-763 (1980).

Rosenthal, K.S. et al. "Mechanism of Action of EM 49, Membrane-Active Peptide Antibiotic" *Antimicrob. Agents Chemother.* 12(6):665-672 (1977).

Rudinger, J., "Characteristics of the amino acids as components of a peptide hormone sequence", *Peptide Hormones*. J. Parsons Edition, University Park Press, pp. 1-7 (Jun. 1976).

Rustici, A. et al. "Molecular Mapping and Detoxification of the Lipid A Binding Site By Synthetic Peptides" *Science* 259:361-365 (1993).

Sakura, et al. "The Contribution of the N-Terminal Structure of Polymyxin B Peptides to Antimicrobial and Lipopolysaccharide Binding Activity" *Bull. Chem. Soc.* Jpn., 77: 1915-1924 (2004).

Salem, et al. "Synthesis of Pelargonoyl-Cyclic Decapeptide Analog of the Antibiotic Polymyxin B1" *Pharmazie*, 35:540-541 (1980).

Schechter, et al. "N-[(2-Sulfo)-9-Fluorenylmethoxycarbonylh-gentamicin Is a Long-Acting Prodrug Derivative" *J. Med. Chem.*, 45:4264-4270 (2002).

Schinzel, P., et al., "The phosphate recognition site of *Escherichia coli* maltodextrin phosphorylase", *Federation of European Biochemical Societies*, 286(1,2): 125-128 (Jul. 1991).

Shechter, et al. "Prolonging the half-life of human interferon-a2 in circulation: Design, preparation, and analysis of (2-sulfo-9-fluorenylmethoxycarbonylh-interferon-a2" *Proc. Nat. Acad. Sci.*, U.S.A., 98(3): 1212-1217 (2001).

Shechter, et al. "Suspensions of pro-drug insulin greatly prolong normoglycemic patterns in diabetic rats" *Biochem. Biophys. Res. Commun.*, 307:315-321 (2003).

Shoji, J. et al. "Isolation of Two New Polymyxin Group Antibiotics (Studies on Antibiotics from the Genus *Bacillus*. XX)" *J. Antibiot.* 30:1029-1034 (1977).

Shoji, J. et al. "The Structure of Polymyxin $S_1$ (Studies on Antibiotics from the Genus *Bacillus*. XXI)" *J. Antibiot.* 30(12):1035-1041 (1977).

Shoji, J. et al. "The Structure of Polymyxin T (Studies on Antibiotics from the Genus *Bacillus*. XXII)" *J. Antibiot.* 30(12):1042-1048 (1977).

Short, E., "Mechanism of Methionine Protection Against the Nephrotoxicity of Polymyxin A", *Brit. J. Pharmacol.*, 7 248-254 (1952).

Sil, D. et al. "Bound to Shock: Protection from Lethal Endotoxemic Shock by a Novel, Nontoxic, Alkylpolyamine Lipopolysaccharide Sequestrant" *Antimicrob. Agents Chemother*. Published online ahead of print on Jun. 4, 2007, pp. 1-32; retrieved from the Internet at www.aac.asm.org on Dec. 1, 2009.

Srinivasa, B.R. et al. "Chemical Modification of Peptide Antibiotics: Part VI—Biological Activity of Derivatives of Polymyxin B" *Indian J. Biochem. Biophys.* 14:54-58 (1978).

Srinivasa, et al. "Essential Amino Groups of Polymyxin B" *Indian J. Biochem. Biophys,*. 17:112-118 (1980).

Sugawara, K. et al. "Bu-2470, a New Peptide Antibiotic Complex. II. Structure Determination of Bu-2470 A, B1, B2a and B2b " *J. Antibiot*. 36:634-638 (1983).

Takeshima, et al. "A deacylation enzyme for Aculeacin A, a neutral lipopeptide antibiotic, from Actinoplanes utahensis: purification and characterization" *J. Biochem.*, 105:606-610 (1989).

Tarr "Improved manual sequencing methods" *Methods Enzymol.*, 47:335-357 (1977).

Trakhanova, M.N., et al., "Structural and Functional Investigation of Polymyxins, Structure and Biological Properties of Polymyxin M Analogs", *All Union Research Institute of Antibiotics*, Moscow, 1: 20-24 (1989).

Trakhanova, M.N., et al., "Structural and Functional Investigation of Polymyxins, Isolation and Properties of Individual Polymyxin M Components", *All Union Research Institute of Antibiotics*, Moscow, 4: 262-266 (1988).

Tsubery, et al. "N-Terminal Modifications of Polymyxin B Nonapeptide and Their Effect on Antibacterial Activity" *Peptides*, 22: 1675-1681 (2001).

Tsubery, H. et al. "Modulation of the Hydrophobic Domain of Polymyxin B Nonapeptide: Effect on Outer-Membrane Permeabilization and Lipopolysaccharide Neutralization" *Mol. Pharmacol*. 62(5):1036-1042 (2002).

Tsubery, H. et al. "Neopeptide Antibiotics That Function as Opsonins and Membrane-Permeabilizing Agents for Gram-Negative Bacteria" *Antimicrob. Agents Chemother*. 49(8):3122-3128 (2005).

Tueber, M. "Preparation of biologically active mono-*N*-acetyl1($^{14}$C)-derivatives of the membrane-specific polypeptide antibiotic polymyxin B" *Z. Naturforsch*. 25b: 117 (1970).

Vaara, M. "The Outer Membrane Permeability-Increasing Action of Linear Analogues of Polymyxin B Nonapeptide" *Drugs Exptl. Clin. Res*. 17(9):437-444 (1991).

Vaara, M. et al. "Novel Polymyxin Derivatives Carrying Only Three Positive Charges Are Effective Antibacterial Agents" *Antimicrob. Agents Chemother*. Published online ahead of print on Jun. 30, 2008, pp. 1-31; retrieved from the Internet at www.aac.asm.org on Dec. 1, 2009.

Velkov, T., et al., "Structure-Activity Relationships of Polymyxin Antibiotics", *J. Med. Chem*, 53(5): 1898-1916 (2010).

Voet, D., et al., "Abnormal Hemoglobins", *Biochemistry Second Edition*, pp. 235-241 (1995).

Vogler, K. et al. "The Chemistry of the Polymyxin Antibiotics" *Experientia* 22(6):345416 (1966).

Wang, W., et al., "Structure and Dynamics of $^{13}$C,$^{15}$N-Labeled Lipopolysaccharides in a Membrane Mimetic", *Angew. Chem. Int. Ed.*, 47: 9870-9874 (2008).

Weinstein, et al. "Selective Chemical Modifications of Polymyxin B" *Biorg. Med. Chem. Lett.*, 8:3991-3996 (1988).

Wilkinson, S., et al., "Structures of the Polymyxins A and the Question of Identity with the Polymyxins M", *Nature*, No. 5059 p. 311 (Oct. 15, 1966).

Witzke N.M. et al. "Broad-Spectrum Derivatives of Polymyxin B and Colistin" *J. Antibiot*. 29(12):1349-1350 (1976).

Written Opinion of the International Searching Authority for International Application No. PCT/US2005/023343 dated Dec. 6, 2006.

Katz, M., et al., "Lipid binding and membrane penetration of polymyxin B derivatives studied in a biomimetic vesicle system", *Biochem J.*, 375: 405-413 (2003).

Tsubery, H. et al. "Structure-Function Studies of Polymyxin B Nonapeptide: Implications to Sensitization of Gram-Negative Bacteria" *J. Med. Chern*. 43:3085-3092 (2000).

Written Opinion of the International Searching Authority for International Patent Application No. PCT/US2009/069247 dated Jun. 23, 2011.

Non Final Office Action for U.S. Appl. No. 11/630,847 dated Mar. 3, 2011.

Notice of Allowance for U.S. Appl. No. 11/630,847 dated Aug. 18, 2011.
International Search Report mailed May 6, 2010, for International Patent Application No. PCT/US2009/069247.
Storm, Daniel R. et al., "Polymyxin and Related Peptide Antibiotics" *Annual Review of Biochemistry*, Palo Alto, vol. 46, Jan. 1, 1977, pp. 723-763.
Castanheira M. et al. "Antimicrobial susceptibility patterns of KPC-producing or CTX-M-producing Enterobacteriaceae,"Microb. Drug Resist.16:61-65 (2010).
Clinical and Laboratory Standards Institute, M07-A8, "Methods for dilution antimicrobial susceptibility tests for bacteria that grow aerobically," approved standard: eighth edition, Wayne, PA: CLSI (2009).
Clinical and Laboratory Standards Institute, M100-S20-U, "Performance standards for antimicrobial susceptibility testing," 20th informational supplement, Wayne, PA: CLSI (2010).
Gales, A.C. et al., "Global assessment of the antimicrobial activity of polymyxin B against 54 731 clinical isolates of Gram-negative bacilli,": report from the SENTRY antimicrobial surveillance programme (2001-2004), Clin Microbiol Infect 12:315-321 (2006).

Giamarellou, H. et al., "Multidrug-resistant Gram-negative infections: What are the treatment options?," Drugs 69(14): 1879-1901 (2009).
Li, J. et al., "Colistin: The re-emerging antibiotic for multidrug resistant Gram-negative bacterial infections," Lancet Infect Dis 6:589-601 (2006).
Livermore, D.M., "Has the era of untreatable infections arrived?," J Antimicrob Chemother 64 Suppl 1:i29-i36 (2009).
Michalopoulos, A. et al.,"Colistin and polymyxin B in critical care," Crit Care Clin 24: 377-391 (2008).
Sader, H.S. et al., "Assessment of colistin and polymyxin B antimicrobial susceptibility testing methods against non-fermentative Gram-negative bacilli (NFGNB)," Abstr. C173, 106TH ASM, Orlando FL (2006).
Tygacil Package Insert, available at www.wyeth.com, accessed Aug. 2009.
Zavascki, A.P. et al., "Polymyxin B for the treatment of multidrug-resistant pathogens: A critical review," J Antimicrob Chemother 60:1206-1215 (2007).

* cited by examiner

ANTIBIOTIC COMPOSITIONS FOR THE TREATMENT OF GRAM NEGATIVE INFECTIONS

RELATED APPLICATIONS

This application claims the benefit of U.S. provisional patent application 61/140,408, filed Dec. 23, 2008, incorporated herein by reference in its entirety.

TECHNICAL FIELD

This application describes antibacterial compounds, and related methods of treatment and methods of manufacture.

BACKGROUND

Gram-negative bacteria that are resistant to aminoglycoside, β-lactam, and fluoroquinolone antibiotics are increasingly common. These bacteria are often only susceptible to the polymyxins and related peptides having antibacterial properties. As a result, there is renewed interest in the use of polymyxins for the treatment of multidrug-resistant gram-negative bacterial infections in humans.

Peptides such as polymyxin B and the related colistin (polymyxin E) have been administered to humans as antibacterial agents. However, their use has been previously limited because of their toxicity. These peptides comprise a seven amino acid cyclic peptide attached to an exocyclic three amino acid chain, wherein the N-terminal amine of the exocyclic chain is linked to a "side chain" or "tail". The tail is an acyl group.

Renal toxicity has been observed with the recommended dosing of polymyxin B in some patients. Neurotoxicity or neuropathy has also been observed in patients with compromised renal functions, with an overall incidence of 7.3% reported in one large study with colistin (see, e.g., Evans, et al. (1999) *Ann. Pharmacother.* 33:960-967). When the acyl exocyclic chain and the adjacent N-terminal 2,4-diaminobutanoic acid (Dab) residue are enzymatically removed from polymyxin, this yields the corresponding polymyxin nonapeptide. The in vivo toxicity of the nonapeptide of polymyxin B is significantly less than that of polymyxin B itself (see, e.g., Kimura, et al. (1992) *J. Antibiot.*, 45, 742-749). The toxicity of the nonapeptide in cell culture is reduced by about 100-fold relative to polymyxin B. However, the antibacterial activity of the nonapeptide is also reduced by about 2-64 fold relative to polymyxin B (see, e.g., Duwe, et al. (1986) *Antimicrob. Agents Chemother,* 30:340-341).

Attempts have been made to chemically modify polymyxin and colistin in order to obtain peptides with improved antibacterial properties and reduced toxicity. For example, the total synthesis of polymyxin B and four analogues was previously accomplished by a combination of solid phase peptide syntheses to obtain linear structures, followed by removal from the resin and condensation in solution at high dilution to obtain the cyclic peptide structure (see, e.g., Tsubery (2001) *Peptides.* 22: 1675-1681). The derivatives, however, were less active than polymyxin B. A more recent total synthesis of polymyxin B and a few closely related compounds was accomplished only by solid phase peptide synthesis (see, e.g., DeVisser, et al. (2003) *J. Peptide Res.* 61, 298-306 and Kline, et al. (2001) *J. Pept. Res.,* 57: 175-187). Although both of these solid phase total synthetic approaches can provide new derivatives of polymyxin, these methods appear limited since the quantities of antibiotic produced are small and require large amounts of amino acid precursors. Any scale up of these methods for clinical studies may prove to be difficult and prohibitively costly. Further, neither of these methods is known to have produced novel derivatives of polymyxin having both improved antibacterial and toxicity properties relative to polymyxin B.

Thus, there is a need for new peptide compounds having equivalent antibacterial properties to polymyxin B, but with significantly lower toxicity, such as renal toxicity, as well as methods of manufacturing such antibacterial compounds.

SUMMARY

Antibacterial compounds of Formula (I) where $R_7$ is an alkyl moiety such as isobutyl or sec-butyl have antibacterial activity against a diverse range of gram negative bacteria with unexpected lower renal toxicity than polymyxin compounds such as polymyxin B.

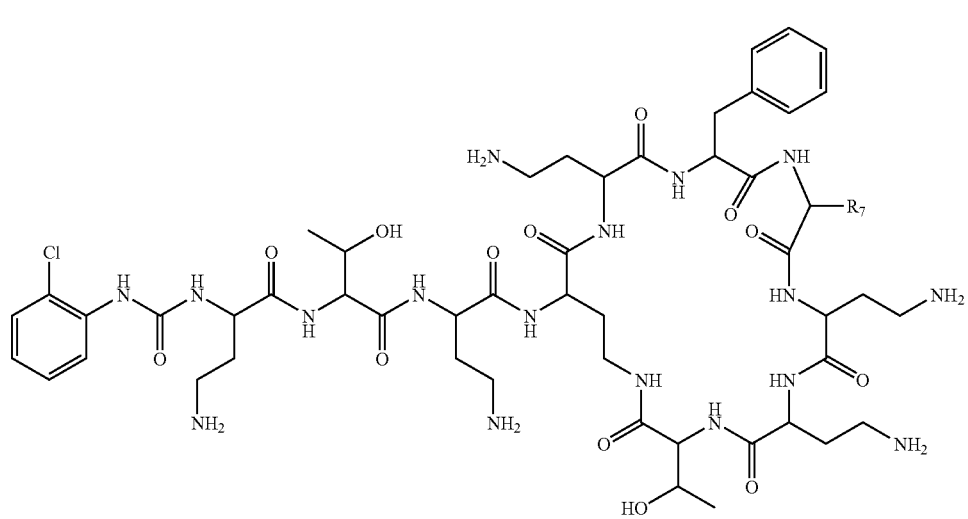

Pharmaceutical compositions containing the antibacterial compounds of Formula (I) are disclosed herein, as well as methods for preparing the antibacterial compounds, amine-protected analogs of the antibacterial compounds, and methods of using the antibacterial compounds. The antibacterial compounds of Formula (I) can be derived from a polymyxin such as polymyxin $B_1$ and [Ile$^7$] polymyxin $B_1$. Pharmaceutical compositions comprising one or more compounds of Formula (I), or pharmaceutically acceptable salts and/or derivatives thereof, are useful, for example, in treating bacterial infections arising from a variety of gram negative pathogens. Methods for treating an infection in a subject can include administering to the subject a therapeutically effective amount of at least one compound of Formula (I), or a pharmaceutically acceptable salt thereof. The antibacterial compounds can also be used in the manufacture of medicaments for treatment of infections.

BRIEF DESCRIPTIONS OF THE FIGURES

DETAILED DESCRIPTION

Definitions

Figure 1:
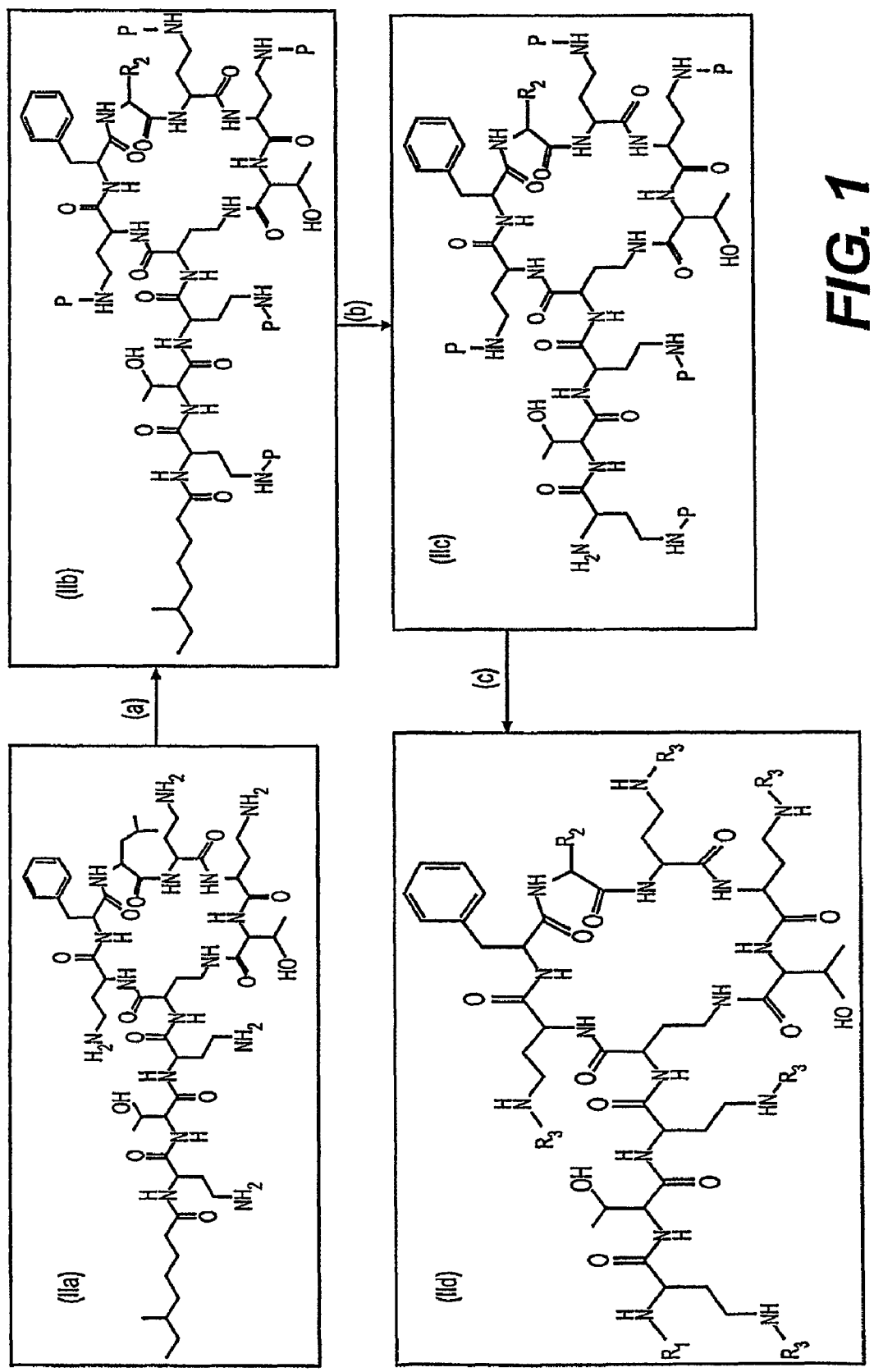
FIG. 1 is a synthetic scheme useful for preparing compounds of Formula (I) and other compounds.

As used herein and unless otherwise indicated, the following words, phrases and symbols shall have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

"Amino protecting group," as used herein, refers to any substituent that may be used to prevent an amino group on a molecule from undergoing a chemical reaction while chemical change occurs elsewhere in the molecule. An amino protecting group can be removed under the appropriate chemical conditions. Numerous amino protecting groups are well known to those skilled in the art, and examples of amino protecting groups, methods for their addition, and methods for their removal can be found in, for example, "Protective Groups in Organic Synthesis" by Theodora W. Greene, John Wiley and Sons, New York, 1991, the disclosure of which is incorporated herein by reference.

"Amino protecting group reagents," as used herein, refer to addition reagents that can react with an amino group such as the N-terminus of a peptide, thereby chemically modifying said amino group by addition of an amino protecting group.

As used herein to refer to an amino protecting group containing at least one "acidic substituent," the term "acidic substituent," refers to a portion of the amino protecting group (e.g., a substituent) containing a donatable hydrogen. Exemplary acidic substituents include the acid form of sulfo, sulfate, sulfonate, carboxy, carboxylate, phosphonate, and phosphate. In one embodiment, the protecting group comprises an aryl or heteroaryl substituted with the acidic substituent.

As used herein, the term "water soluble" refers to the compound with sufficient water solubility for an intended purpose. Water soluble compounds with an amino protecting group with an acidic substituent can have a first water solubility adequate to permit deacylation of such compounds in an aqueous medium (e.g., 0.1-5 g/L, preferably about 1 g/L or higher). Similarly, water soluble antibiotic compounds can have a second water solubility adequate to permit dissolution of therapeutically effective amounts of the antibiotic compounds in an aqueous pharmaceutical composition (e.g., about 100-500 g/L, including at least about 300 g/L).

"Aryl," as used herein, refers to a mono-, bi-, or other multi-carbocyclic, aromatic ring system, including aromatic ring systems fused to one or more rings selected from aryl, cycloalkyl, and heterocyclyl, as well as aryl moieties having from 5-14 ring members. Nonlimiting examples of aryl groups include phenyl, naphthyl, biphenyl, and anthracenyl.

"Carboxy," as used herein, refers to a COOH radical.

"Fmoc" is a 9-fluorenylmethoxycarbonyl group.

"Halo," as used herein, refers to bromo, chloro, fluoro, and iodo, and the term "halogen" includes fluorine, chlorine, bromine, and iodine.

"Heteroaryl," as used herein, refers to mono-, bi-, or other multi-carbocyclic, aromatic ring systems having from one to four non-carbon atoms or hetero groups containing one or more non-carbon atoms or groups selected from O, N, NH, S, or SO forming a portion of at least one position in the aromatic ring system. Heteroaryl ring systems can have, for example, five to fifteen ring members. Nonlimiting examples of heteroaryl groups include indolyl, pyridinyl, thiazolyl, thiadiazoyl, isoquinolinyl, pyrazolyl, oxazolyl, oxadiazolyl, triazolyl, and pyrrolyl groups.

"[Ile$^7$]-polymyxin B$_1$," as used herein, refers to a compound of the Formula:

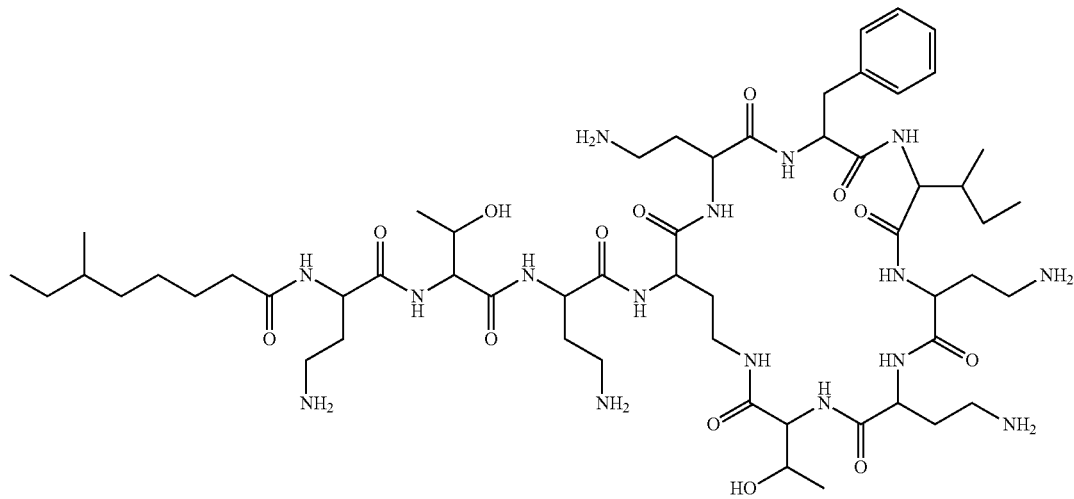 [SMILES: CCC(C)CCCCC(=O)NC(CCN)C(=O)NC(C(=O)NC(CCN)C(=O)NC1CCNC(=O)C(C(C)O)NC(=O)C(CCN)NC(=O)C(CCN)NC(=O)C(C(C)CC)NC(=O)C(Cc2ccccc2)NC(=O)C(CCN)NC1=O)C(C)O]

commercially available salts thereof, such as a sulfate salt.

"Polymyxin B$_1$," as used herein, refers to a compound of the Formula:

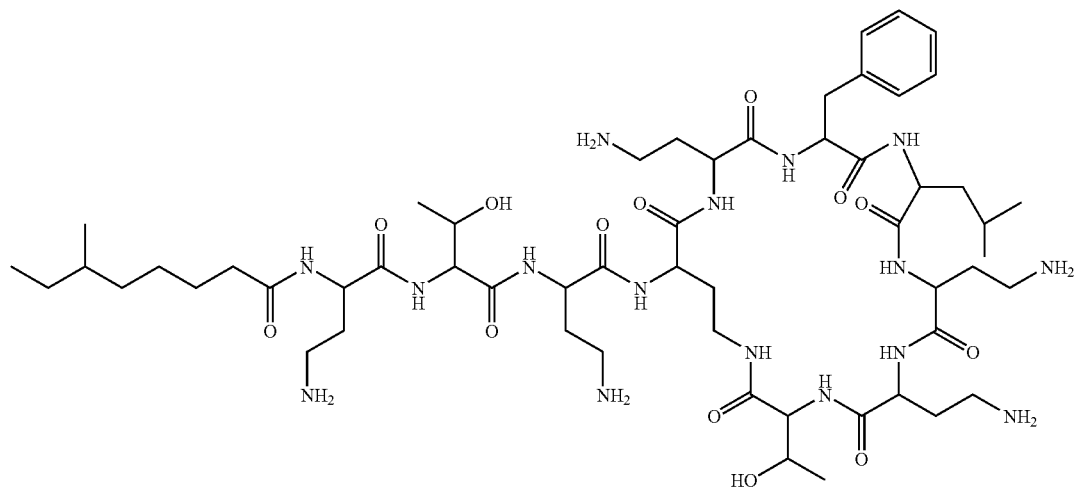 [SMILES: CCC(C)CCCCC(=O)NC(CCN)C(=O)NC(C(=O)NC(CCN)C(=O)NC1CCNC(=O)C(C(C)O)NC(=O)C(CCN)NC(=O)C(CCN)NC(=O)C(CC(C)C)NC(=O)C(Cc2ccccc2)NC(=O)C(CCN)NC1=O)C(C)O]

and commercially available salts thereof, such as a sulfate salt.

"Sulfo," as used herein, refers to the —SO$_3$H moiety.

The term "prodrug," as used herein, represents compounds that are rapidly transformed in vivo to the parent compound of the antibacterial compounds described herein, for example, by hydrolysis in blood. A discussion is provided in T. Higuchi and V. Stella, *Pro-drugs as Novel Delivery Systems*, Vol. 14 of the ACS Symposium Series, and in Edward B. Roche, ed., *Bioreversible Carriers in Drug Design*, American Pharmaceutical Association and Pergamon Press, 1987, both of which are incorporated herein by reference.

The term "pharmaceutically acceptable prodrugs" as used herein, represents those prodrugs of the compounds of the present invention that are, within the scope of sound medical judgment, suitable for use in an intended therapeutic application (e.g., suitable for contact with the tissues of humans and lower animals) without undue toxicity, irritation, allergic response, commensurate with a reasonable benefit/risk ratio, and effective for their intended use, as well as the ionic (e.g. zwitterionic) forms and pharmaceutically acceptable derivatives (e.g., esters) of antibacterial compounds.

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art, such as a sulfate salt. For example, S. M. Berge, et al. describes pharmaceutically acceptable salts in *J. Pharm. Sci.*, 1977, 66:1-19.

As used herein, the phrase "pharmaceutically-acceptable carrier" refers generally to solvents, dispersion media, excipients, coatings, matrices, stabilizers, buffers, absorption enhancers, adjuvents, controlled release media, and the like, that are compatible with an intended use, such as pharmaceutical administration. The use of such carriers for pharmaceutically active substances is well known in the art. Nonlimiting examples of carriers include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

The term "therapeutically effective amount," as used herein refers to an amount of an antibacterial compound that is effective to perform the function being sought by the researcher or clinician without unduly harming the tissues of the subject to which the agent is administered.

The term "subject," as used herein, refers to a mammal, a plant, a lower animal, or a cell culture. In one embodiment, a subject is a human or other animal patient in need of antibacterial treatment.

Unless otherwise indicated, the following abbreviations as used herein have the following meanings:
AUC=area under the curve
ADME=absorption, distribution, metabolism, excretion
BID=bis in die, meaning to give medication twice a day
BUN=blood urea nitrogen
cfu=colony forming units
CH$_3$CN=acetonitrile
Cmax=the maximum plasma concentration
CV=cardiovascular
CYP=Cytochrome P450
EC50=half maximal effective concentration
ED=effective dose
EDTA=ethylenediaminetetraacetic acid
EtOH=ethanol
HOAc=acetic acid
HPLC=high pressure liquid chromatography
MeOH=methanol
MIC=minimum inhibitory concentration to inhibit growth of the test organism
MIC90=MIC required to inhibit growth of 90% of the strains of an organism tested
MTD=maximum tolerated dose
NaH$_2$PO$_4$=sodium phosphate
NOAEL=no observable adverse effect level
PK=pharmacokinetics
PMB=polymyxin B
PME=polymyxin E (colistin)
QD=quaque die (every day)
TID=ter in die, meaning to give medication three times a day
OD$_{600}$=optical density measured at 600 nm Antibacterial Compounds Antibacterial compositions can include compounds of Formula (I) where R$_7$ is an alkyl moiety selected from isobutyl and sec-butyl, as well as pharmaceutically acceptable derivatives or pharmaceutically acceptable salts thereof:

(I)
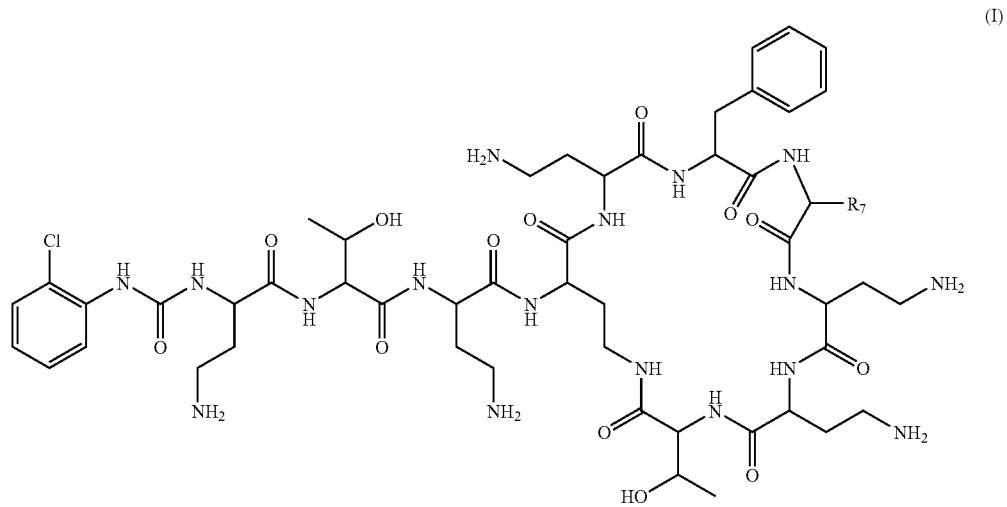
For example, pharmaceutical compositions with antibacterial activity can include one or more compounds of Formula (I), such as a compound of Formula (Ia), a compound of Formula (Ib), specific enantiomers of Formula (Ia) or Formula (Ib), or any combination thereof, or pharmaceutically acceptable salts (e.g., a sulfate salt) or derivatives (e.q., esters) thereof:
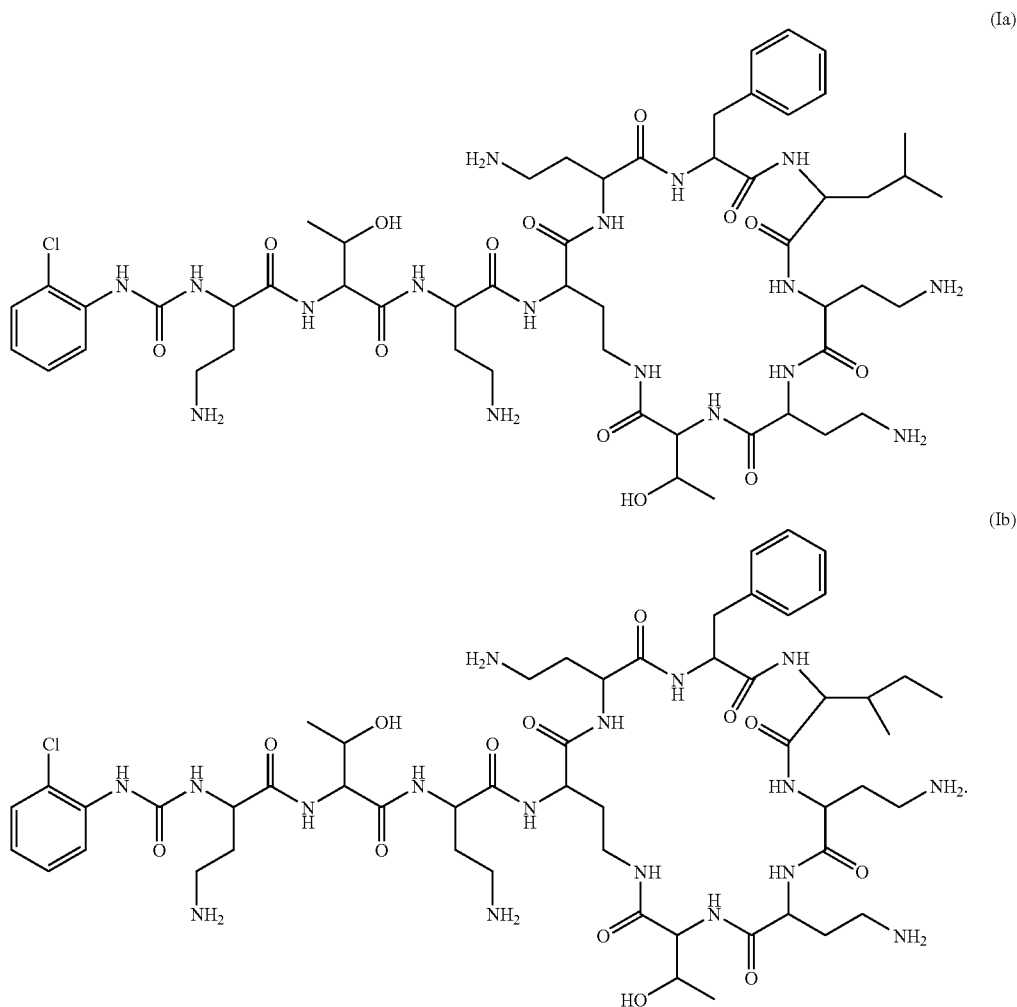

One particular example of an antibacterial compound of Formula (Ia) is described by Formula (Ic) and Formula (Ic') below.

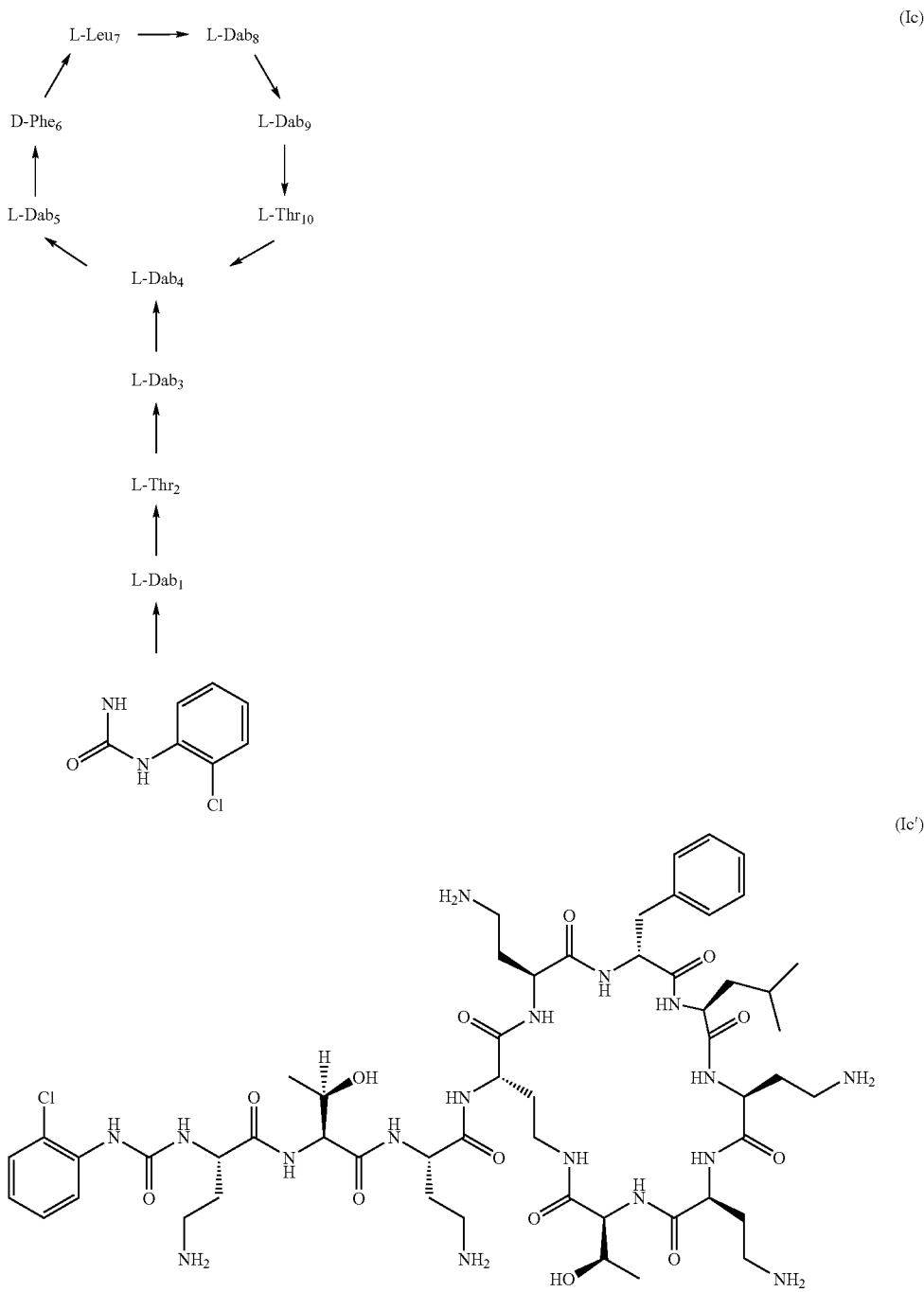

(Ic)

(Ic')

The antibacterial compounds of Formula (I) have antibacterial activity against a range of gram negative bacteria, including antibacterial activity and spectrum similar to certain polymyxin compounds such as colistin (polymyxin E) and/or polymyxin B. For example, as discussed in the Examples, compounds of Formula (I) are active against colistin susceptible *P. aeruginosa* and *Acinetobacter* spp., including multi-drug resistant strains, while also having antibacterial activity against *E. coli, K. pneumonia, Citrobacter* spp.

and some activity against *Enterobacter* spp. isolates. As detailed in the Examples, pharmacological studies confirmed in vivo antibacterial activity of a compound of Formula (I) comparable to polymyxin B in both a murine lung infection model using *P. aeruginosa* #44 and *K. pneumoniae* bacteria #21, as well as a murine thigh infection model using *A. baumannii* #1570. In addition, the compounds of Formula (I) are as active or more active than polymyxin B against multi-drug resistant bacteria. Furthermore, the compound of Formula (I) designated as compound 5 in the examples below, is as active as polymyxin B against a bacterial infection that may be caused or exacerbated by *P. aeruginosa*. One preferred antibacterial compound of Formula (I) is (S)-4-amino-N-((2S,3R)-1-((S)-4-amino-1-oxo-1-((3S,6S,9S,12S,15R,18S,21S)-6,9,18-tris(2-aminoethyl)-15-benzyl-3-((R)-1-hydroxyethyl)-12-isobutyl-2,5,8,11,14,17,20-heptaoxo-1,4,7,10,13,16,19-heptaazacyclotricosan-21-ylamino)butan-2-ylamino)-3-hydroxy-1-oxobutan-2-yl)-2-(3-(2-chlorophenyl)ureido)butanamide.

Surprisingly, the antibacterial compounds of Formula (I) have reduced toxicity compared to other compounds of Formula (II) and polymyxins such as polymyxin B. For example, certain compounds of Formula (I) (i.e., compounds 5 and 6 in Table 1) were substantially less toxic in the rat kidney proximal tubule cell culture cytotoxicity assay of Example 4 than either polymyxin B or the structurally similar 3-chlorophenyl analog designated compound 4. Compounds 5 and 6 of Formula (I) have an EC50 value of >1,000 μg/mL compared to EC50 values of 318 μg/mL measured for polymyxin B and 691 μg/mL measured for compound 4. The Formula (I) compound designated compound 5 in Table 1 also showed reduced renal toxicity compared to polymyxin B in the seven-day repeat dose safety study in cynomologus monkeys detailed in Example 6.

Synthesis of Compounds

The compounds of Formula (II), including the compounds described in Formula (I), can be prepared from a polymyxin starting material according to the synthetic scheme shown in FIG. 1:

compositions thereof. Unless otherwise indicated, the compounds disclosed herein can be utilized as a single isomer or as a mixture of stereochemical isomeric forms. For example, compounds of Formula (Ia) can include compounds of Formula (Ic) and Formula (Ic') and/or other diastereomers described by Formula (Ia).

Compounds of Formula (II) can be obtained from any suitable lipopeptide starting material of Formula (III) comprising a cyclic portion with a plurality of 2,4-diaminobutanoic acid residues and an acyl exocyclic tail portion (T):

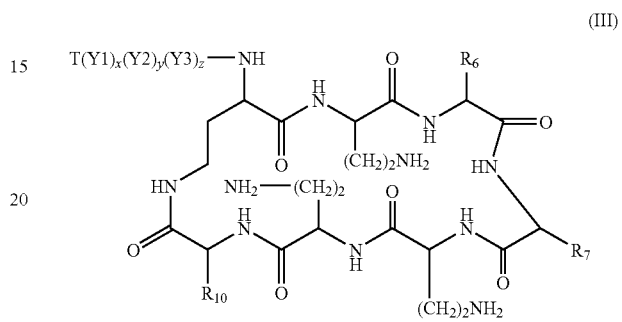

(III)

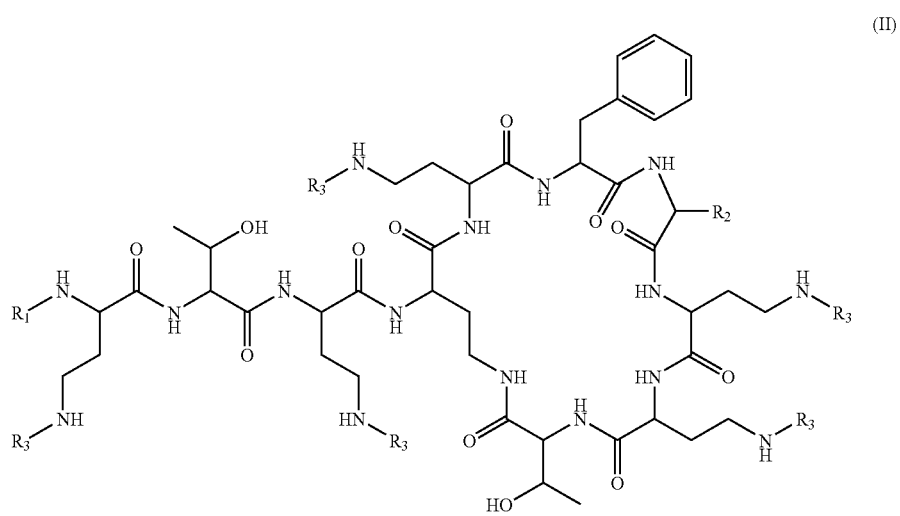

(II)

wherein:
R$_1$ is chosen from H, and —C(O)NHR$_A$, wherein R$_A$ is chosen from benzyl and phenyl, and wherein both said benzyl and phenyl may be optionally substituted with one or more halo and/or nitro;
R$_2$ is chosen from —CH$_2$CH(CH$_3$)$_2$ and —CH(CH$_3$)CH$_2$CH$_3$; and
R$_3$ is H.

As shown in the Examples, certain compounds of Formula (II) are as active or more active against bacteria than polymyxin B. Compounds of this embodiment include those designated as compounds 1, 2, 3, 4, 5, 6, 7, 8, 9, 10, 11, 13, 14, and 15 in the Examples below.

The compounds of Formula (II) can possess one or more chiral asymmetric carbon atoms and are thus capable of exhibiting optical activity. Unless otherwise indicated, Formula (II) describes racemic and individual enantiomeric and/or diastereomeric forms of compounds at each chiral position, including racemic or enantiomerically resolved non-racemic wherein Y1 and Y3 are 2,4-diaminobutanoic acid residues; Y2 is a threonine residue; x, y and z are integers independently equal to 1; R$_6$ is benzyl; R$_7$ is chosen from isobutyl and sec-butyl; and R$_{10}$ is 1-hydroxy-1-ethyl; T is R'—(C=O)—; and R' is an alkyl or (e.g., hydroxyl-) substituted alkyl, such as 6-methyloctanoyl, 6-methylheptanoyl, octanoyl, heptanoyl, nonanoyl, or 3-hydroxy-6-methyloctanoyl. Examples of suitable starting materials include a polymyxin B, or a [Ile$^7$]-polymyxin B. The starting material can be a naturally occurring polymyxin compound isolated from the fermentation of *Bacillus polymyxa* according to procedures described in, e.g., Hausmann, et al. (1954) *J. Am. Chem. Soc.* 76, 4892-4896.

Referring to FIG. 1, the polymyxin B1 starting material (IIa) is reacted with an amino protecting group reagent (step (a)) to form a protected starting material (IIb) comprising an amino protecting group (P) attached to the primary amino moieties in the starting material (IIa). Preferably, the amino protecting group (P) comprises an acidic moiety to provide a protected starting material (IIb) that is sufficiently water soluble to react with a deacylating agent in an aqueous medium (step (b)) to form a deacylated material (IIc). The deacylated material (IIc) can be reacted with an addition reagent (step (c)) to form a protected antibacterial compound (IId). The amino protecting group (P) can be removed from the protected antibacterial compound (IId) to form the compound of Formula (II), including compounds of Formula (I).

The water solubility of the compounds of Formulae (IIa), (IIb), (IIc), (IId) and Formula (I) may differ, while each independently being suitable for different intended purposes. For example, a water soluble protected starting material (e.g., compound of Formula (IIb) in FIG. 1) can include amino protecting groups with an acidic substituent (e.g., "P" in Formula (IIb) in FIG. 1) providing sufficient water solubility to perform enzymatic deacylation (e.g., step (b) in FIG. 1) of the protected starting material at an acceptable yield in an aqueous medium. A product material can be an antibiotic compound of Formula (I) with sufficient water solubility to form an aqueous pharmaceutical composition comprising a therapeutically effective concentration of the compound of Formula (I).

The protecting group (P) can be selected to provide a desired level of water solubility in the protected starting material (IIb). For example, the protecting group (P) can include an aryl or heteroaryl moiety and at least one acidic substituent selected from carboxy, sulfo, sulfate, and salts thereof. Exemplary protecting groups include 9-fluorenylmethoxycarbonyl (Fmoc) substituted with acidic substituents or salts thereof, such as 2-sulfo-9-fluorenylmethoxycarbonyl ($HSO_3$-Fmoc), and its sodium salt ($NaSO_3$-Fmoc), 2-carboxymethyl-9-fluorenylmethoxycarbonyl (2-carboxymethyl-Fmoc), 2-carboxy-9-fluorenylmethoxycarbonyl (2-carboxy-Fmoc), and 4-carboxy-9-fluorenylmethoxycarbonyl (4-carboxy-Fmoc). Preferably, the protecting group is a sulfonic acid of 9-fluorenylmethoxycarbonyl, such as 2-sulfo-9-fluorenylmethoxycarbonyl. Additional amino protecting groups include, but are not limited to, the protecting groups disclosed in "Protective Groups in Organic Synthesis" by Theodora W. Greene, John Wiley and Sons, New York, 1991 at pp. 315-348, the disclosure of which is incorporated herein by reference.

The protected starting material (IIb) can be reacted with an enzymatic deacylating agent in an aqueous medium to form the deacylated material (IIc). One example of a deacylating enzyme useful for deacylation of the protected starting material (IIb) is produced by certain microorganisms of the genus family Actinoplanaceae. Some of the known species and varieties of this family include *Actinoplanes philippinensis, Actinoplanes armeniacus, Actinoplanes utahensis, Actinoplanes missouriensis, Spirillospora albida, Streptosporangium roseum, Streptosporangium vulgare, Streptosporangium roseum var hollandensi, Streptosporangium album, Streptosporangium viridialbum, Amorphosporangium auranticolor, Ampullariella regularis, Ampullariella campanulata, Ampullariella lobata, Ampullariella digitata, Pilimelia terevasa, Pimelia anulata, Planomonospora parontospora, Planomonospora venezuelensis, Planobispora longispora, Planobispora rosea, Dactylosporangium aurantiacum,* and *Dactylosporangium thailandende*. All natural and artificial variants and mutants which are obtained from the Actinoplanacea family and which produce the enzyme may be used in this invention. The deacylating agent is preferably a polymyxin deacylase enzyme, which can be obtained from *Actinoplanes utahensis*.

The deacylase enzyme can be obtained as a water-soluble freeze-dried solid. In one embodiment, the deacylase is obtained by fermenting *Actinoplanes utahensis*, separating the cells from the fermentation medium, washing the cells with water, extracting the cells with basic buffer at pH 8-11 for about 20 minutes, adjusting the extract to pH 7-8 and freeze-drying. The powdered form of the enzyme resulting from this process can be relatively stable and can be readily re-dissolved in water for use. Further purification can be obtained by gel filtration, membrane filtration or other types of chromatography. This enzyme can deacylate, for example, a sodium salt N-[2-sulfo-9-fluorenylmethoxycarbonyl]$_5$ polymyxin B to obtain the deacylated protected peptide having the Formula (IIc) in FIG. 1. In other embodiments, the enzyme from *Actinoplanes utahensis* can be used as the whole broth from the fermentation or as the washed cells.

The enzyme from *Actinoplanes utahensis* can also be used as a water-solubilized preparation. The water-solubilized enzyme preparation can be obtained by a relatively strong basic extraction of the washed cells, followed by adjustment of the pH of the clear extract to pH 7-8. This water-solubilized enzyme preparation can be freeze-dried to a solid form.

Referring to step (c) of FIG. 1, the deacylated material (IIc) is reacted with an addition reagent selected to react with a primary amino group at the N-terminus of the exocyclic portion of the deacylated material (IIc), thereby chemically modifying the amino group by addition of all, or a component, of the addition reagent to the amino group. For example, an addition reagent may be an acylamino reagent such as R'—(C=O)-LG or a sulfonating reagent such as R'—$SO_2$-LG, where LG is a leaving group, that can react with an amino group. An addition reagent may also be, for example, an isocyanate, isothiocyanate, activated ester, acid chloride, sulfonyl chloride, activated sulfonamide, activated heterocycle, activated heteroaryl, chloroformate, cyanoformate, thioacylester, phosphoryl chloride, phosphoramidate, imidate, or lactone. An addition reagent may also.be an aldehyde or ketone that reacts with an amine under reductive conditions to form an alkylated amine. An addition reagent may also be an activated amino acid, or an amino acid and a peptide coupling reagent, such as, e.g., PyBOP® (behzotriazole-1-yl-oxy-trispyrrolidino-phosphonium hexafluorophosphate), HBtU (2-(1H-benzotriazole-1-yl)-1,1,3,3-tetramethyluronium hexafluorophosphate), HBtU/HOBt (2-(1H-benzotriazole-1-yl)-1,1,3,3-tetramethyluronium hexafluorophosphate/N-hydroxybenzotriazole), or DCC (dicyclohexylcarbodiimide). In the addition reaction shown in step (c) of FIG. 1, various addition reagents can be selected to reactively couple the functional substituent "$R_1$-" to the primary amine in the deacylated material (IIc) to form compounds of Formula (II), where $R_1$ is defined in Table 1 of the Examples.

The protected antibacterial compound (IId) in FIG. 1 can be converted to a compound of Formula (II) by removing the protecting groups (P) of the protected antibacterial compound (IId) (e.g., by deprotection using standard methods such as those described in "Protective Groups in Organic Synthesis" by Theodora W. Greene, John Wiley and Sons, New York, 1991, the disclosure of which is incorporated herein by . reference). As those skilled in the art will recognize, the choice of amino protecting group employed in the first step of the process (step a) will dictate the reagents and procedures used in removing said amino protecting group. When the reagent for the chemical modification contains one or more protecting group(s), those protecting group(s) can also be removed. The choice of the protecting group(s) utilized on the chemical modifying agent substituent(s) will dictate the reagents and procedures used in removing said protecting group(s). When the protecting group(s) utilized on the modifying agent substituent(s) and the protecting group utilized for the protected compounds are compatible, the protecting groups may be removed in a single step. However, when the protecting group(s) are incompatible multiple steps may be required to remove all of the protecting groups.

After removal of the amino protecting groups (P), the compounds of Formula (I) can be purified by gel filtration, chromatography, or reverse-phase HPLC. Diastereomers can be separated by conventional means such as chromatography or crystallization. Enantiomers can be obtained by resolution of the racemic mixtures according to conventional processes, for example by formation of diastereomeric salts by treatment with an optically active acid or base. Nonlimiting examples of appropriate acids include tartaric, diacetyltartaric, dibenzoyltartaric, ditoluoyltartaric and camphorsulfonic acid. The mixture of diastereomers can be separated by crystallization followed by liberation of the optically active bases from the optically active salts. Alternative process for separation of enantiomers include the use of a chiral chromatography column optimally chosen to maximize the separation of the enantiomers, or the use of supercritical fluid chromatography (SFC). For example, the compound of Formula (Ic) can be obtained from a starting material with corresponding stereochemical structures (e.g., a polymyxin $B_1$ starting material). Another method involves synthesis of covalent diastereomeric molecules by treating compounds of the invention with an activated form of an enantiomerically enriched acid or with an enantiomerically enriched isocyanate. The synthesized diastereomers can be separated by conventional means such as chromatography, distillation, crystallization or sublimation, and then hydrolyzed to obtain the enantiomerically enriched compound. Optically active compounds can likewise be obtained by utilizing optically active starting materials. These isomers may be in the form of a free acid, a free base, an ester or a salt.

One particular process for preparing an antibacterial compound can include the following steps: (a) treating a polymyxin such as polymyxin B with an amino protecting group comprising at least one acidic substituent to form a protected compound; (b) treating the protected compound with a deacylating agent, to form at least one deacylated protected compound having the Formula:

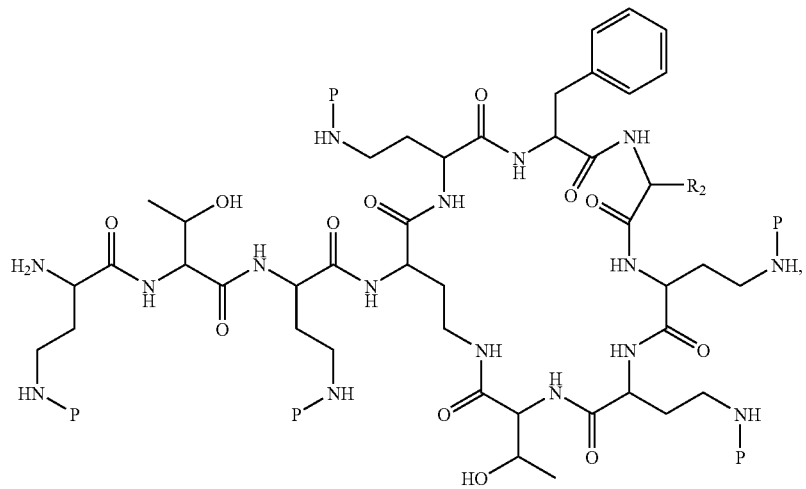

wherein $R_2$ is isobutyl and P is an amino protecting group;
(c) treating the at least one deacylated protected compound with an isocyanate to form at least one acylated protected compound having the Formula:

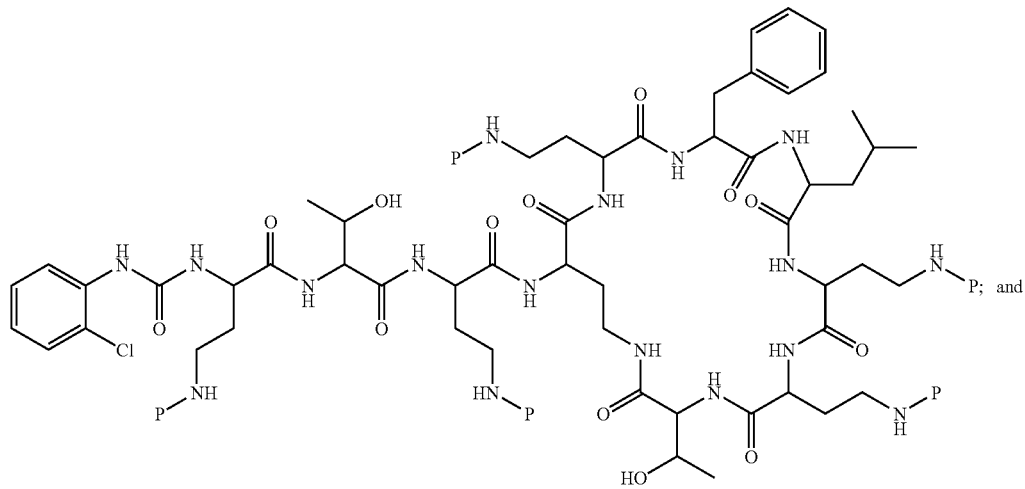

(d) removing the amino protecting groups (e.g., by treating the at least one acylated protected compound with an organic base) to form the antibacterial compound having the Formula:

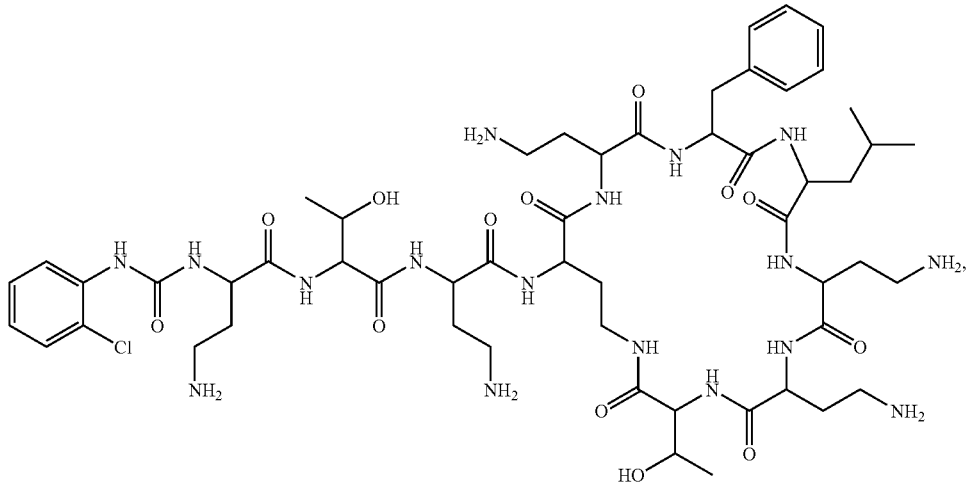

such as a compound of Formula (Ic) and Formula (Ic') above.

The Examples describe one suitable method for obtaining the antibacterial compound of Formula (Ic) and (Ic'). Purification of the antibacterial compounds by the methods of Examples using HPLC can provide a compound of Formula (Ic) and (Ic') with a purity of about 98% (e.g., with up to about 1% of Formula (Ib)). Alternatively, similar methods using low pressure liquid chromatography can be used to produce an antibacterial compound of Formula (Ic) and Formula (Ic') with a purity of about 92% (e.g., with up to about 3% of a compound of Formula (Ib)).

Pharmaceutical Antibacterial Compositions

Pharmaceutical compositions can be formed by combining a compound of Formula (I) or a pharmaceutically acceptable derivative or salt thereof with a pharmaceutically acceptable carrier suitable for delivery to a recipient subject (e.g., a human) in accordance with known methods of drug delivery. Antibacterial pharmaceutical compositions suitable for administration of one or more compounds of Formula (I) can be Formulated. The compound of Formula (I), and/or pharmaceutically acceptable salts or derivatives of Formula (I) can be included in a pharmaceutical antibacterial composition along with one or more carriers.

A compound of Formula (I) can be Formulated as a variety of salts or derivatives to improve stability or toxicological properties of the compound, increase or decrease solubility, improve pharmacokinetic performance of the compound (e.g., $C_{max}$ or AUC measurements) or improve storage properties (e.g., to reduce hygroscopicity) of a pharmaceutical composition. Pharmaceutically-acceptable salts of compounds of Formula (I) may be prepared by conventional means from the corresponding compound of the invention by treating, for example, the compound with the appropriate acid or base. Examples of publications describing the selection and formation of pharmaceutically acceptable salts of medicinal compounds include Haynes, Delia A., et al., "Occurrence of Pharmaceutically Acceptable Anions and Cations in the Cambridge Structural Database," Journal of Pharmaceutical Sciences, v. 94, no. 10, 2111-2120 (October 2005), and Stahl, P H, et al., Eds., "Handbook of Pharmaceutical Salts: Properties, Selection and Use," Weinheim/Zurich, Wiley-VCHNHCA, incorporated herein by reference.

A compound of Formula (I) may also be Formulated as a prodrug in a pharmaceutical composition. Pro-drugs can include an antibacterial compound disclosed herein having one or more amino groups protected with $HSO_3$-Fmoc and/or other amino protecting groups (comprising at least one acidic group are antibacterial pro-drugs (e.g., as shown as "P" in compounds of Formula (IId) in FIG. 1). The $HSO_3$-Fmoc group can be cleaved after introduction into an animal, such as, e.g., a mammal, including a human, liberating the biologically active compound. Administration of a biologically active compound as the protected pro-drug may result in a slow release mechanism for the antibacterial compound. Other suitable prodrugs can include esters of a compound of Formula (I). A discussion of pro-drugs is provided in, e.g., Gershonov, et al. (2000), *J. Med. Chem.* 43: (13), 2530-2537, and Schechter, et al. (2002), *J. Med. Chem.* 45: (19), 4264-4270, which are all incorporated by reference.

The pharmaceutical compositions can be formulated for parenteral delivery, including intravenous, intramuscular, intraperetoneal, subcutaneous, intraocular, intrathecal, intraarticular, intrasynovial, cisternal, intrahepatic, intralesional and intracranial injection, infusion, and/or inhaled routes of administration for the therapeutic treatment of medical conditions, such as bacterial infections.

Pharmaceutical preparations can be prepared in accordance with standard procedures and are administered at dosages that are selected to treat infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical composition can include one or more carriers, as defined above, for an intended medical use. Pharmaceutical compositions for parenteral injection comprise pharmaceutically-acceptable aqueous or nonaqueous solutions of antibacterial compounds of Formula (I) in addition to one or more of the following: pH buffered solutions, adjuvants (e.g. preservatives, wetting agents, emulsifying agents, and dispersing agents), liposomal Formulations, nanoparticles, dispersions, suspensions or emulsions as well as sterile powders for reconstitution into sterile injectable solutions or dispersions just prior to use. In one particular example, a pharmaceutical composition includes an antibacterial active component with about 92-98% w/w of the active component being a compound of Formula (Ic) and Formula (Ic'), and with about 0-3% (including about 0-1%, 0-3%, 1-3%, up to 1%, and/or up to 3%) w/w of the active component being a compound of Formula (Ib), where this active component is added to the other components of the pharmaceutical composition. One particular intravenous Formulation is formed by combining an antibacterial active component with the remaining components of an intravenous pharmaceutical composition, where the active component has about 98% w/w of a compound of Formula (Ic) and Formula (Ic') and about 0-1% w/w of a compound of Formula (Ib). For intravenous (IV) use, the pharmaceutical composition can include any of the commonly used intravenous fluids that can be administered by infusion, such as physiological saline or Ringer's solution. Injectable depot forms to release the antibacterial agent in situ can be made by forming microencapsulating matrices of the drug in biodegradable polymers such as polylactide-polyglycolide. Depending upon the ratio of drug to polymer and the nature of the particular polymer employed, the rate of drug release can be controlled. For intramuscular preparations, a sterile Formulation of a compound of the present invention, or a suitable soluble salt form of the compound, for example the hydrochloride salt, can be dissolved and administered in a pharmaceutical diluent such as Water-for-Injection (WFI), physiological saline or 5% glucose.

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

The injectable Formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

The pharmaceutical compositions can be in powder form for reconstitution in the appropriate pharmaceutically acceptable carrier at the time of delivery. In another embodiment, the unit dosage form of the compound can be a solution of the antibacterial compound of Formula (I), or a salt thereof, in a suitable diluent in sterile, hermetically sealed ampoules or sterile syringes.

Methods of Using Antibacterial Compositions

The antibacterial compounds described herein are useful in the manufacture of antibacterial pharmaceutical compositions, and treatment of bacteria with these compositions. In particular, the antibacterial compounds are useful in treating and eliminating gram negative bacterial infections. Methods of treating bacterial infections in subjects (e.g., humans and animals) can include the administration of a therapeutically effective amount of an antibiotic compound of the Formula (I) or a pharmaceutically acceptable salt or prodrug thereof.

The antibacterial compounds of Formula (I) can be used in vivo, for example, to treat bacterial infections in a subject, as well as in vitro, for example to treat cells (e.g., bacteria) in culture to eliminate or reduce the level of bacterial contamination of a cell culture. In one embodiment, at least one compound of Formula (I), or pharmaceutical compositions thereof, are administered to a cell culture, such as by administering in a nutrient medium.

Methods of treatment of such infections include administering to a subject in need thereof a therapeutically effective amount of an antibacterial compound of Formula (I). The compound can be parenterally administered to a subject having or suspected to have a bacterial infection, such as a gram negative infection.

The antibacterial compounds of Formula (I) are preferably used in vivo to treat an infection in a subject by administering a therapeutically effective amount of a compound of Formula (I) in a pharmaceutical composition. The method can comprise parenterally administering to a subject in need thereof a pharmaceutical composition comprising at least one compound of Formula (I). Pharmaceutical compositions include compositions comprising compound(s) of Formula (I) in an amount sufficient to achieve the intended purpose, i.e., the treatment or prevent of infectious diseases. The amount and concentration of antibacterial compound of Formula (I) in the pharmaceutical composition, as well as the quantity of the pharmaceutical composition administered to a subject, can be selected based on clinically relevant factors, such as medically relevant characteristics of the subject (e.g., age, weight, gender, other medical conditions, and the like), the solubility of the antibacterial compound in the pharmaceutical composition, the potency and activity of the antibacterial compound, and the manner of administration of the pharmaceutical composition. A pharmaceutical composition comprising a therapeutically effective amount of an antibacterial compound of Formula (I) can be administered intravenously to a patient for treatment of gram negative infections in a clinically safe and effective manner, including one or more separate administrations of the composition. For example, about 0.05 mg/kg to about 5.0 mg/kg can be administered to a subject per day in one or more doses (e.g., doses of about 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain antibiotic indications, the total daily dose of a compound of Formula (I) can be about 0.05 mg/kg to about 3.0 mg/kg of one or more compounds of Formula (I) administered intravenously to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 mg/kg/day of a compound of Formula (Ia), Formula (Ic) or Formula (Ic') using 60-minute QD, BID or TID intravenous infusion dosing. In one particular example, antibiotic pharmaceutical compositions can be administered to a subject with, e.g., total daily doses of 1.5 mg/kg, 3.0 mg/kg, 4.0 mg/kg of a composition with up to about 92-98% of Formula (Ia), Formula (Ic) and/or Formula (Ic') are intravenously administered QD or BID. The amount per administered dose or the total amount administered will depend on such factors as the nature and severity of the infection, the age and general health of the patient, the tolerance of the patient to the compound and the microorganism or microorganisms involved in the infection.

In particular, the pharmaceutical compositions comprising antibacterial compounds of Formula (I) can be used to treat a subject having a bacterial infection in which the infection is caused or exacerbated by a gram-negative bacteria. These gram-negative bacteria include, but are not limited to, *Acinetobacter* spp. (including *Acinetobacter baumannii*), *Citrobacter* spp., *Enterobacter* spp., *Escherichia* spp. (including *Escherichia coli*), *Haemophilus influenzae, Morganella morganii, Pseudomonas aeruginosa, Klebsiella* spp. (including *Klebsiella pneumoniae*), *Salmonella* spp., *Shigella* spp., *Yers-*

*inia pseudotuberculosis*, and all species of *Enterobacter, Pasteurella, Brucella, Bordetella, Proteus, Serratia, Providencia,* and *Edwardsiella*. The bacteria infection can also be caused or exacerbated by a gram-negative bacteria chosen from *Pseudomonas aeruginosa, Acinetobacter* spp, *Stenotrophomonas maltophilia, Escherichia coli, Klebsiella pneumoniae, Citrobacter* spp, and *Enterobacter*. In one embodiment, at least one compound of Formula (I) may be used to treat multiple drug resistant bacteria, such as Multiple Drug Resistant (MDR) *P. aeruginosa*, Extended Spectrum Beta Lactamase (ESBL) *K. pneumonia*, ESBL *E. coli*, and *A. baumannii*

The pharmaceutical compositions can be used to treat a bacterial infection of any organ or tissue in the body caused by gram-negative bacteria. These organs or tissue include, without limitation, skeletal muscle, skin, bloodstream, kidneys, heart, lung and bone. For example, a pharmaceutical composition comprising at least one compound of Formula (I) can be administered to a subject to treat, without limitation, skin and soft tissue infections (e.g., complex skin infections), bacteremia, interabdominal infections and urinary tract infections (e.g., cUTI). In addition, a compound of Formula (I) may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *H. influenzae*. At least one compound of Formula (I) can be administered to a subject to treat mixed infections that comprise different types of gram-negative bacteria, or which comprise both gram-positive and gram-negative bacteria. These types of infections include intra-abdominal infections and obstetrical/gynecological infections. At least one compound of Formula (I) may also be administered to a subject to treat an infection including, without limitation, endocarditis, nephritis, septic arthritis, intra-abdominal sepsis, bone and joint infections and osteomyelitis. At least one compound of Formula (I), or pharmaceutical compositions thereof, may also be directly injected or administered into an abscess, ventricle or joint. Pharmaceutical compositions administered as an aerosol for the treatment of pneumonia or other lung-based infections. In one embodiment, the aerosol delivery vehicle is an anhydrous, liquid or dry powder inhaler.

EXAMPLES

A series of compounds according to Formula (II) were prepared, as described herein:

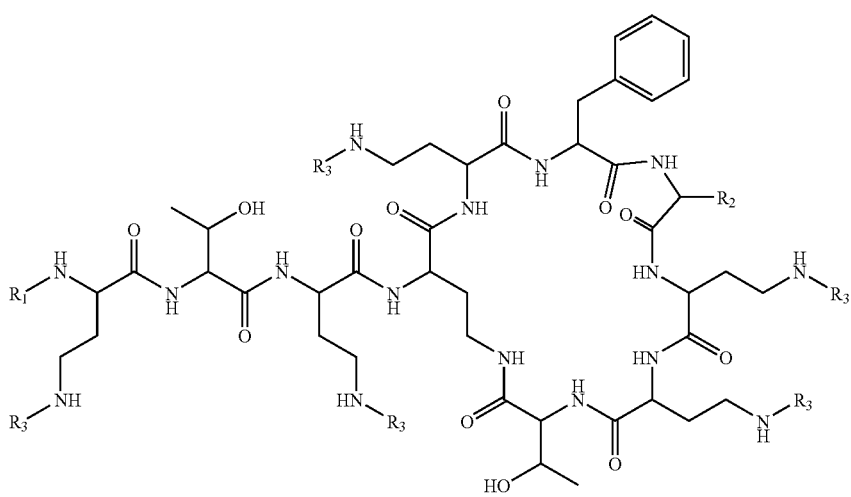

(II)

wherein the substituents are selected as indicated in Table 1. These compounds include compounds of Formula (I) (designated Compound 5 and Compound 6) and Formula (II).

TABLE 1

Compounds of Formula (II), including compounds of Formula (I)

| Compound No. | $R_1$ | $R_2$ | $R_3$ |
|---|---|---|---|
| 1 | —C(O)NH-phenyl | —$CH_2CH(CH_3)_2$ | H |
| 2 | —C(O)NH-phenyl | —$CH(CH_3)CH_2CH_3$ | H |
| 3 | —C(O)NH-4-chlorophenyl | —$CH_2CH(CH_3)_2$ | H |
| 4 | —C(O)NH-3-chlorophenyl | —$CH_2CH(CH_3)_2$ | H |
| 5 | —C(O)NH-2-chlorophenyl | —$CH_2CH(CH_3)_2$ | H |
| 6 | —C(O)NH-2-chlorophenyl | —$CH(CH_3)CH_2CH_3$ | H |
| 7 | —C(O)NH-2,6-dichlorophenyl | —$CH_2CH(CH_3)_2$ | H |
| 8 | —C(O)NH-2,6-dichlorophenyl | —$CH(CH_3)CH_2CH_3$ | H |
| 9 | —C(O)NH-4-bromophenyl | —$CH_2CH(CH_3)_2$ | H |
| 10 | —C(O)NH-4-fluorophenyl | —$CH_2CH(CH_3)_2$ | H |
| 11 | —C(O)NH-pentafluorophenyl | —$CH_2CH(CH_3)_2$ | H |
| 12 | —C(O)NH-2-chlorobenzyl | —$CH_2CH(CH_3)_2$ | H |
| 13 | —C(O)NH-2-chlorobenzyl | —$CH(CH_3)CH_2CH_3$ | H |
| 14 | —C(O)NH-2,4-dichlorobenzyl | —$CH_2CH(CH_3)_2$ | H |
| 15 | —C(O)NH-2,4-dichlorobenzyl | —$CH(CH_3)CH_2CH_3$ | H |
| 16 | —C(O)NH-2-chloro-4-nitrophenyl | —$CH_2CH(CH_3)_2$ | H |
| 17 | —C(O)NH-2-chloro-4-nitrophenyl | —$CH(CH_3)CH_2CH_3$ | H |
| 18 | —C(O)NH-phenyl | —$CH_2CH(CH_3)_2$ | $HSO_3$-Fmoc |

TABLE 1-continued

Compounds of Formula (II), including compounds of Formula (I)

| Compound No. | $R_1$ | $R_2$ | $R_3$ |
|---|---|---|---|
| 19 | —C(O)NH-phenyl | —CH(CH$_3$)CH$_2$CH$_3$ | HSO$_3$-Fmoc |
| 20 | —C(O)NH-4-chlorophenyl | —CH$_2$CH(CH$_3$)$_2$ | HSO$_3$-Fmoc |
| 21 | —C(O)NH-3-chlorophenyl | —CH$_2$CH(CH$_3$)$_2$ | HSO$_3$-Fmoc |
| 22 | —C(O)NH-2-chlorophenyl | —CH$_2$CH(CH$_3$)$_2$ | HSO$_3$-Fmoc |
| 23 | —C(O)NH-2-chlorophenyl | —CH(CH$_3$)CH$_2$CH$_3$ | HSO$_3$-Fmoc |
| 24 | —C(O)NH-2,6-dichlorophenyl | —CH$_2$CH(CH$_3$)$_2$ | HSO$_3$-Fmoc |
| 25 | —C(O)NH-2,6-dichlorophenyl | —CH(CH$_3$)CH$_2$CH$_3$ | HSO$_3$-Fmoc |
| 26 | —C(O)NH-4-bromophenyl | —CH$_2$CH(CH$_3$)$_2$ | HSO$_3$-Fmoc |
| 27 | —C(O)NH-4-fluorophenyl | —CH$_2$CH(CH$_3$)$_2$ | HSO$_3$-Fmoc |
| 28 | —C(O)NH-pentafluorophenyl | —CH$_2$CH(CH$_3$)$_2$ | HSO$_3$-Fmoc |
| 29 | —C(O)NH-2-chlorobenzyl | —CH$_2$CH(CH$_3$)$_2$ | HSO$_3$-Fmoc |
| 30 | —C(O)NH-2-chlorobenzyl | —CH(CH$_3$)CH$_2$CH$_3$ | HSO$_3$-Fmoc |
| 31 | —C(O)NH-2,4-dichlorobenzyl | —CH$_2$CH(CH$_3$)$_2$ | HSO$_3$-Fmoc |
| 32 | —C(O)NH-2,4-dichlorobenzyl | —CH(CH$_3$)CH$_2$CH$_3$ | HSO$_3$-Fmoc |
| 33 | —C(O)NH-2-chloro-4-nitrophenyl | —CH$_2$CH(CH$_3$)$_2$ | HSO$_3$-Fmoc |
| 34 | —C(O)NH-2-chloro-4-nitrophenyl | —CH(CH$_3$)CH$_2$CH$_3$ | HSO$_3$-Fmoc |
| 35 | H | —CH$_2$CH(CH$_3$)$_2$ | HSO$_3$-Fmoc |
| 36 | H | —CH(CH$_3$)CH$_2$CH$_3$ | HSO$_3$-Fmoc |

Unless otherwise indicated, the antibacterial activities of compounds are indicated in the Examples as their minimum inhibitory concentrations (MICs) against *Pseudomonas aeruginosa, Acinetobacter* spp, *Stenotrophomonas maltophilia, Escherichia coli, Klebsiella pneumoniae, Citrobacter* spp, and *Enterobacter*. MICs can be determined by the conditions disclosed in the Examples, as well as in Jarolmen, H. et al., "Activity of Minocycline Against R-Factor Carrying Enterobacteriaceae," *Infectious Immunity*, Vol. 1, No. 4, pp. 321-326, 1970, the disclosure of which is incorporated herein by reference.

Accordingly, MIC's refer to-the concentration of each antimicrobial agent required to inhibit the growth of a bacterial isolate, as well as the corresponding concentrations required to inhibit 50% and 90% of each group of microorganisms tested (MIC$_{50}$ and MIC$_{90}$, respectively, consistent with definitions in the "Instructions to Authors" for *Antimicrobial Agents and Chemotherapy* (Antimicrobial Agents and Chemotherapy, January 2010, p. 1-23, Vol. 54, No. 1, incorporated herein by reference). When only up to nine isolates of a species are tested, MIC's are reported as the MIC range of each antimicrobial agent tested. MIC values provided as numerical ranges for testing of a single bacteria strain indicate the range of MIC values obtained in repeated tests of the indicated bacteria strain.

Example 1

Preparation of the Deacylase

The deacylase is produced by culturing *Actinoplanes utahensis* NRRL 12052 under submerged aerobic fermentation conditions. The fermentation protocol employed is known (Boeck, L. D. et al., Journal of Antibiotics 41:(8), 1085-1092 (1998), incorporated herein by reference). A stock culture of the NRRL 12052 variant, preserved in 20% glycerol at −70° C., was introduced into a 25×150 mm test tube with a glass rod and Morton closure containing 10 mL of a medium composed of sucrose 2.0%, pre-cooked oatmeal 2.0%, distiller's grains and solubles 0.5%, yeast extract 0.25%, K$_2$HPO$_4$ 0.1%, KCl 0.05%, MgSO$_4$.7H$_2$O 0.05% and FeSO$_4$.7H$_2$O 0.0002% in deionized water. After incubation at 30° C. for 72 hrs on a rotary shaker orbiting at 250 rpm the resulting mycelial suspension was transferred into 50 mL of PM3 medium in a 250 mL Erlenmeyer flask. This medium contained sucrose 2.0%, peanut meal 1.0%, K$_2$HPO$_4$ 0.12%, KH$_2$PO$_4$ 0.05% and MgSO$_4$.7H$_2$O 0.025% in tap water. The flask was incubated at a temperature of 30° C. for a period of 60 to 90 hrs. The harvest time was determined by an assay which involved HPLC analyses of the deacylation of N-[2-sulfo-9-fluorenlymethoxycarbonyl]$_5$ polymyxin B by the whole broth at different times during the fermentation.

Because single-colony isolates from a lyophile of the culture were heterogeneous for both morphology and enzyme production capability, selections were made to recover a stable, high-producing variant. Initially, multiple fermentations were carried out using inocula prepared from strain 12052. Vegetative growth from the flask yielding the best deacylating activity was plated on a differential agar (CM). CM agar contained corn steep liquor 0.5%, Bacto peptone 0.5%, soluble starch 1.0%, NaCl 0.05%, CaCl$_2$.2H$_2$O 0.05% and Bacto agar 2.0%. Colonies were then selected for further evaluation. Isolate No. 18 was selected as a small colony type and shown to be the best deacylase producer of all colonies selected. Comparison was based on conversion of protected polymyxin B to deacylated protected polymyxin B as determined by HPLC. This isolate was routinely used for the production of the deacylase enzyme.

Example 2

Preparation of Compounds of Formula I

Step (a): Preparation of Penta-9-(2-sulfo)fluorenyl-methoxycarbonyl-Polymyxin B

Fluorenylmethoxycarbonyl N-hydroxysuccinimide (1.1982 g, 3.55 mmol) dissolved in 15 mL of methylene chloride was stirred in an ice bath, using a drierite tube to maintain a dry atmosphere. A solution of chlorosulfonic acid (0.21 mL, 3.15 mmol) in 6 mL of methylene chloride was added dropwise to give a yellow solution. The mixture was allowed to come to room temperature and stirred for several hours. The resulting white precipitate was filtered and washed with cyclohexane-methylene chloride (1:1) then dried in vacuo over phosphorus pentoxide to afford 9-(2-sulfo)fluorenylmethoxycarbonyl N-hydroxysuccinimide (HSO$_3$Fmoc-O-Su). Yield 1.148 g, (hygroscopic white solid). See, e.g., Y. Shechter et al. J. Med. Chem., 43, 2530 (2000).

Polymyxin B, containing a mixture of polymyxin B$_1$ and [Ile$^7$] polymyxin B$_1$ (1.0 g, 0.841 mmol), as purchased from Sigma-Aldrich, was dissolved in a solution of 25 mL saturated sodium bicarbonate, 25 mL of water and 25 mL of tetrahydrofuran. A solution of 2-sulfo-9-fluorenylmethoxy-N-hydroxysuccinimide (2.0 g, 4.8 mmol) in 25 mL of tetrahydrofuran was added in several portions over 45 min. The reaction mixture was stirred at room temperature overnight and diluted with 50 mL of water. The reaction mixture was then acidified to pH 0.5-1 with approximately 30 mL of 6N hydrochloric acid to give an oily precipitate. The mixture was chilled overnight and the aqueous layer was decanted. The oily residue was dissolved in 100 ml of ethanol and the ethanol was evaporated in vacuo (35° C.) with the aid of ethyl acetate. The resulting solid was triturated with ethyl acetate, filtered and dried to afford 1.74 g of a mixture containing the protected polymyxin $B_1$ and [$Ile^7$] polymyxin $B_1$ products.

The above procedure can be used with the corresponding polymyxin B sulfate salt (containing a mixture of polymyxin $B_1$ sulfate and [$Ile^7$] polymyxin $B_1$ sulfate) and 2-sulfo-9-fluorenylmethoxycarbonyl chloride with similar results.

Step (b): Deacylation of Penta-2-sulfo-9-fluorenylmethoxycarbonyl-Polymyxin B

Penta-2-sulfo-9-fluorenylmethoxycarbonyl-Polymyxin B (1 g) was dissolved in 800 mL of 0.02 M ammonium phosphate buffer (pH 7.2), combined with 200 mL EtOH and 7.44 g EDTA, and then adjusted to pH 8 with 1 N NaOH. The EtOH and EDTA were added to prevent some conversion to the protected nonapeptide and to act as a preservative. To this resulting solution was added 25 mg of deacylase enzyme and the reaction was run at pH 8 and stirred at 30° C. for 8-16 hours. The reaction was then adjusted to pH 6 with 1 N HCl and the protected polymyxin B decapeptide was added to the resin as described in the next section. The resulting filtrate contains the enzyme.

The completed 1 L deacylation reaction solution was adjusted to pH 6. Envi-Chrom P resin was added, the mixture was stirred for 1 hour, and the resin was removed by filtration. The resin was placed in a column, washed with 80 mL of 20% $CH_3CN$ in 0.02 M $NaH_2PO_4$ adjusted to pH 6.8 with approximately 40 mL of 22.5% $CH_3CN$ in the buffer and 80 mL of 25% $CH_3CN$ in the buffer. The deacylated protected Compounds 69 and 70 were then eluted from the resin with 40% $CH_3CN$ in the buffer as 8 mL fractions were collected. Fractions 4, 5, and 6 were combined, evaporated to remove $CH_3CN$, and the residual aqueous solution was freeze dried to obtain 704 mg of crude product mixture. The crude product mixture was mixed with 20 mL of MeOH, stirred for 0.5 hours, and separated by centrifugation. The decant was evaporated to dryness, water was added to the residue, and the solution was freeze dried to obtain 452 mg of deacylated protected Compounds 69 and 70 as a very light tan powder. This product mixture contained about 85% of the deacylated protected Compound 35 and 15% of the deacylated protected Compound 36.

Step (c): Acylation of deacylated protected Compounds 69 and 70

The deacylated protected mixture of Compounds 69 and 70, 412 mg (approximately 0.16 mmol) was dissolved at room temperature in 4 mL of dimethylformamide (DMF) and 0.4 mL collidine/2M HCl (5:1 volume ratio) to yield a clear solution which was sampled for HPLC as 0-time reaction reference. To the stirred solution was slowly added 80 μL (0.66 mmol) of 2-chlorophenylisocyanate. After stirring for 30 minutes at room temperature, the reaction was sampled by analytical HPLC and was found to contain approximately 100% conversion to desired acylated protected Compounds 22 and 23 as a mixture.

Step (d): Deprotection of the acylated protected Compounds 22 and 23

To the reaction mixture in Step (c) was added 1.6 mL MeOH (to reduce mixture viscosity) and 0.4 mL piperidine to remove the protecting groups. The mixture was stirred for 60 minutes at room temperature. The reaction mixture was diluted with 80 mL of Solvent A (see below) plus 0.28 mL HOAc (to ensure neutralization of excess piperidine), to yield a clear solution which contained the deprotected products of Formula (I), which were designated as Compound 5 (i.e., $R_7$ is isobutyl) and Compound 6 (i.e., $R_7$ is sec-butyl).

Example 3

Isolation and Purification of Compounds 5 and 6

Preparation of CM-sepharose Cartridge

Fast Flow a carboxymethyl agarose (e.g. sold under the tradename, CM-SEPHAROSE) slurry (100 mL sample) was diluted with approximately 100 mL of 20% EtOH. Approximately 30 mL of the dilute slurry was poured into a 60 mL polypropylene solid phase extraction tube and the slurry was allowed to settle. The top frit was carefully put in place to exclude air bubbles to obtain final packing bed dimensions of 22×26.5 mm. The excess 20% EtOH was decanted and the packing was rinsed by gravity flow with 60 mL of Solvent A.
Product Isolation The diluted reaction mixture was applied to the cartridge and allowed to flow in by gravity. The product-loaded cartridge was rinsed with 60 mL Solvent A and then rinsed with 24 mL of 0.05 M ammonium acetate at pH 5.0. The cartridge was stripped with 32 mL of 0.27 M sodium sulfate pH 2.3 buffer (1:2 dilution of Stock Buffer A, see below). 4 mL fractions (#4 through #11) were collected and analyzed by HPLC to evaluate product content profile. Fractions 7 through 10 (containing approximately 99% of a mixture of compound 5 and compound 6) were pooled.
Purification by Preparative HPLC The column was rinsed at room temperature at 10 mL/min with 100 mL each, in order, Eluent A, Eluent B, Eluent D and Eluent C. The pooled CM-Sepharose fractions were injected onto the column with two sequential injections, approximately 8 mL each, each being rinsed onto the column with 50 mL of Eluent C at 5.0 mL/min. The gradient was then initiated and all elutions were done at room temperature. The column eluate was monitored at 281 nm (approximately 1 cm flow cell path length). Fraction collection was initiated as Compound 6 started to elute. 7.5 mL fractions were collected until the apex of the major peak followed by 3 mL fraction collection. Fractions were evaluated by analytical HPLC and the appropriate fractions were pooled. Fractions 8-10 contained Compound 6 and fractions 14-29 contained essentially pure Compound 5.
Product Desalting and Freeze Drying The desalting cartridge was prepared as follows: 2.0 g of EnviChrom-P styrene/divinylbenzene resin was slurried in 20 mL of 50% acetonitrile then poured into a 20 mL polypropylene cartridge. The top frit was put in place and the excess 50% acetonitrile was drained off. Using gravity flow for all subsequent steps, the packing was rinsed with 24 mL of 67% acetonitrile and then 24 mL of distilled water. Preparative HPLC fractions 14 through 29 were pooled and the acetonitrile was removed under vacuum at below 35° C. The desolventized fraction pool was applied to the cartridge and the loaded resin was rinsed with multiple 2 mL then 4 mL increments of distilled water (16 mL total). The desalted product was stripped from the resin using 48 mL of 67% acetonitrile. The acetonitrile was removed from the strip fraction under vacuum at below 35° C. and the desolventized product solution was freeze dried to obtain 119 mg of Compound 5, which appeared to be pure by analytical HPLC. The preparative HPLC fractions containing Compound 6 were treated in a similar manner to obtain 15 mg of Compound 6, which also appeared pure by analytical HPLC.

Solvent A: 65% MeOH 0.04M ammonium acetate/0.02M acetic acid pH 5.0, 650 mL HPLC grade MeOH, 40 mL 1.00M ammonium acetate/0.50M acetic acid, pH 5.0 (1:10 dilution), and distilled water to 1.00 L.

Stock Buffer A: approximately 0.54 M in total sulfate (as sodium sulfate/bisulfate) pH 2.3 (1:10 dilution), 55.3 g (30 mL) concentrated sulfuric acid, 76.4 g (50 mL) 50% NaOH (approximately 20M), and distilled water to 1.00 L.

Preparative HPLC Conditions

Equipment: Waters Prep 4000 pump with Radial-Pak compression unit, Waters Delta-Pak C18 radial-pak cartridges (100 A pore, 2.5×21 cm), ABI 757 UV Detector with heat exchanger removed, 10 mL Loop injector, and Pharmacia fraction collector.

Eluent A: 100% isopropanol, Eluent B: 20% isopropanol

Eluent C: 15% acetonitrile 0.04M in sodium sulfate (pH 2.3) 150 mL acetonitrile, 80 mL Stock Buffer A, and distilled water to 1.00 L.

Eluent D: 30% acetonitrile 0.04M in sodium sulfate (pH 2.3) 300 mL acetonitrile, 80 mL Stock Buffer A, and distilled water to 1.00 L.

| Elution Gradient: | | | |
| --- | --- | --- | --- |
| Time (min) | % Eluent C | % Eluent D | Flow (mL/min) |
| 0 | 100 | 0 | 10.0 |
| 45 | 67 | 33 | 10.0 |
| 45.1 | 67 | 33 | 5.0* |

*Note:
flow rate is reduced to accommodate limitation of fraction collector

Additional compounds were produced using procedures similar to those described above in Examples 1-3 from the corresponding commercially available isocyanates.

Example 4

Elucidation of Formula (Ic) and (Ic') Chemical Structure

The chemical structure of Formula (Ic) and (Ic') (designated Compound 5) was determined to include a 2-chlorophenyl carbamyl linked to the N-terminal 2,4-Diaminobutyric acid of a 10-amino acid peptide. The C-terminal residue of Compound 5, threonine, is linked to the molecule via an amide bond on the a-amino side chain of 2,4-diaminobutyric acid, and the compound contains 10 amino acids which are 6 residues of 2,4-diaminobutyric acids, 2 residues of threonine, and one each of leucine and phenylalanine. The compound has an average molecular weight of 1216.82 with an empirical Formula of $C_{54}H_{86}N_{17}O_{13}Cl$.

The structure shown in Formula (Ic') was deduced based on the method of synthesis from known starting materials and confirmed by HPLC and spectroscopic measurements.

UV-visible spectroscopy was used to determine the electronic absorption of Compound 5. In water, one maximum absorption wavelength was detected. The maximum absorption wavelength is 236 nm with an extinction coefficient of 10565 M-1 cm$^{-1}$. The UV-VIS spectrum of Compound 5 was acquired on Agilent 8543 UV-Visible system. The spectrum was collected in the absorbance mode. The light-path length used was 1 cm. Compound 5 was dissolved in water at the final concentration of 0.0735 mg/mL prior to the measurement. From the UV-Visible spectrum, one maximum wavelength was observed at 236 nm. The calculated extinction coefficient of Compound 5 at 236 nm was 10565 $M^{-1}cm^{-1}$ Infrared spectroscopy was used to characterize the functional groups present in the Compound 5 molecule. The Compound 5 FTIR sample was prepared and measured by a KBr method. The Compound 5 infrared spectrum was acquired on a Perkin-Elmer 1600 Series FTIR. The spectrum was recorded between 400 cm$^{-1}$ and 4000 cm$^{-1}$. The major bands observed in the IR spectrum are 3271.7 cm$^{-1}$, associated with the amide, amine, and hydroxy (OH) stretches, the 3066.8 and 2929.6 cm$^{-1}$ vibrations due to the asymmetric and symmetric CH stretching (aromatic and aliphatic respectively), the 1652.1 and 1539.0 cm$^{-1}$ stretches, associated to the amide I and II band, and finally the 1108.0 cm$^{-1}$ band, associated to the alcoholic CO stretches.

The exact mass of Compound 5 was found to be 1216.6350 Da ([M+H]+, Theoretical, 1216.6352 Da). The exact mass of Compound 5 was measured by positive ion electrospray high-resolution mass spectrometry on Micromass Q-Tof API US hybrid quadrupole/time of flight mass spectrometer. The MS/MS data of Compound 5 was recorded in the positive ionization mode by nanospray ionization on a Sciex Q-Star/ Pulsar hybrid quadrupole/time-of-flight mass spectrometer. For MS/MS experiments, the m/z 608.86 ion, assigned as [M+2H]2+ was selected. The y-type ion observed at m/z 762.5 is consistent with the structure of the cyclic peptide portion of the Compound 5. The y-type ions at m/z 963.6 and 989.6 are consistent with the presence of the two amino-acid residues, which is attached to the cyclic peptide. Signals at m/z 662.5, 561.4, 461.3, and 361.3 are consistent with the sequence of amino acids in the cyclic peptide of Compound 5. An intense signal at m/z 254.1 is consistent with the presence of the $ClC_6H_4NHCONHCH(CH_2CH_2NH_2)CO$ acyl peptide at the N-terminus of the Compound 5. Other signals e.g., m/z 202.1, 302.2 and 101.1 support the sequential assignment of Compound 5. This amino acid sequence information confirmed that Compound 5 is composed of 10 amino acid residues.

Amino acid analysis of Compound 5 was determined by reversed phase HPLC combined to acid hydrolysis and derivatization with AccQ fluorescence reagent (6-amino-quinolyl-N-hydroxysuccinimidyl carbamate). Derivatized amino acids were excited at 250 nm and monitored at 395 nm. Compound 5 contains 10 amino acids. The amino acid compositions (ratio) are summarized as follows: Threonine (2.0); 2,4-diaminobutyric acid (5.7); Leucine (1.1); and Phenylalanine (1.1). The amount of 2,4-diaminobutyric acid residues in Compound 5 were found to be 5.7 residues, which is slightly less than the expected amount (6 residues). This is due to partial hydrolysis of a urea group in Compound 5. This result was consistent with the data from MS/MS analysis.

The amino acid sequence of Compound 5, confirmed with tandem mass spectroscopy and NMR (2D NOESY), falls into the following order: 2-chlorophenyl carbamyl-1Dab-2Thr-3Dab-4Dab-5Dab-6Phe-7Leu-8Dab-9Dab-10Thr, where 4Dab was linked to 10Thr forming a cyclic peptide. The amino acid composition (ratio) of Compound 5 was determined by amino acid analysis. Stereochemistry of amino acid constituents in Compound 5 was determined by LCMS using Marfey's reagent. The peptide was transformed into its amino acid constituents by hydrolysis under acidic conditions. Each amino acid was derivatized with Marfey's reagent and analyzed by LC/MS. The amino acid stereochemistry of Compound 5 hydrolysate was observed and compared to the individual derivatized amino acid reference standards.

Determination of amino acid stereochemistry was achieved by LC retention time and mass identification of each derivatized amino acid using TM-146. The complete amino acid assignment of Compound 5 is the following: N-2-chlorophenylcarbamyl-N2-L-(2,4)-Dab-L-Thr-N2-L-(2,4)-Dab-N2-(4-&)-L-(2,4)-Dab-N2-L-(2,4)-Dab-D-Phe-L-Leu-N2-L-(2,4)-Dab-N2-L-(2,4)-Dab-L-Thr(&). The 1H, COSY, TOCSY and NOESY data were primarily used to assign $^1$H peaks, while $^{13}$C, $^{13}$C DEPT, HSQC and HMBC were used to assign $^{13}$C data, and to verify $^1$H assignment. The results from NMR, consistent with data obtained from MS and AAA, confirm the structure of Compound 5.

Nuclear magnetic resonance spectra were acquired at 5° C. on a 600 MHz instrument at Custom NMR Services (Ayer, Mass.). One-dimensional spectra and two-dimensional COSY, TOCSY (mixing time 60 ms), NOESY (mixing time 150 ms), HSQC, HMBC were obtained for Compound 5 reference standard lot CG-01-003. The sample was dissolved in 150 mM sodium phosphate buffer, pH 6.5 with 90% $H_2O$ and 10% $D_2O$ to a concentration of 58 mg/mL.

The $^1$H, COSY, TOCSY and NOESY data were primarily used to assign $^1$H peaks, while $^{13}$C, $^{13}$C DEPT, HSQC and HMBC were used to assign $^{13}$C data, and to verify $^1$H assignment. The sequential identification of residues in Compound 5 was executed through the analysis of two-dimensional NOESY spectra. Compound 5 exhibits NOE peaks from backbone NH of one residue to the side chain of the preceding residue which enables the sequential identification of residues. Table 2A gives the proton and carbon chemical shift assignments of the backbone and side chains of Compound 5.

TABLE 2A $^1$H and $^{13}$C peak Assignments for Compound 5 at 5° C.

| Residue | NH | C=O | αH (αC) | βH | Others |
|---|---|---|---|---|---|
| Tail* | 8.06 | 157.03 | | | 6.98 (127.53), 6.87 (126.72), 7.15 (128.95), 6.90 (128.28), C—NH 133.31, C—Cl not observable |
| Dab1 | 7.11 | 173.67 | 4.11 (51.24) | 1.78, 1.93 (28.38) | γH 2.83 (35.82) |
| Thr2 | 8.15 | 171.86 | 4.01 (58.63) | 3.93 (66.30) | γH 0.90 (18.20) |
| Dab3 | 8.43 | 172.29 | 4.15 (50.51) | 1.86, 1.75 (27.60) | γH 2.72 (35.80) |
| Dab4 | 8.31 | 172.50 | 3.90 (50.80) | 1.55 (29.61) | γH 3.05, 2.80 (35.60), δNH 7.44 |
| Dab5 | 8.28 | 171.43 | 4.19 (49.76) | 1.78, 1.68 (29.03) | γH 2.63, 2.56 (35.43) |
| Phe6 | 8.62 | 173.17 | 4.12 (55.98) | 2.62, 2.84 (35.60) | 7.19 (125.65), 7.15 (128.95), 7.05 (128.28), 6.87 (126.14), γC 134.42 |
| Leu7 | 8.42 | 174.52 | 3.81 (50.80) | 1.10, 0.95 (38.15) | γH 0.03 (22.22), δH1 0.32 (21.80), δH2 0.23 (19.40) |
| Dab8 | 7.90 | 170.96 | 3.99 (51.37) | 1.95 (27.40) | γH 2.87, 2.78 (35.43) |
| Dab9 | 8.31 | 173.01 | 3.89 (52.43) | 1.61, 1.88 (27.94) | γH 2.74 (35.81) |
| Thr10 | 7.89 | 171.23 | 3.92 (65.43) | 3.80 (59.18) | γH 0.87 (18.51) |

*Tail: 2-chlorophenylcarbamyl

Compound 5 has the physical properties listed in Table 2B.

TABLE 2B

| Appearance: | White to off white amorphous solid |
|---|---|
| Odor: | Odorless |
| pH: | 5.9, at 5 mg/mL in water |
| Melting/boiling range: | 260° C. |
| Dissociation constant (pKa): | 8.17, 8.62, 9.01, 9.41 and 9.71 |
| Specific rotation: | −107° |
| Solubility Profile: | >300 g/L in water |
| | 0.2 g/L in ethanol |
| Lipophilicity (Log P) | <−1.0 |
| Hygroscopicity: | Very hygroscopic |
| Crystallinity: | Non-crystalline powder |
| Salt form: | Sulfate salts |

Example 5

Microbiology Studies

To evaluate the potency and spectrum of compounds of Formula (I), (i.e., Compounds designated 5 and 6), a study was conducted that put together a panel of 455 Gram negative strains, which included multi-drug resistant clinical isolates selected from various surveillance programs. Table 3A lists the strains that were included in the study and the activity of Compound 5, Compound 6, and colistin (polymyxin E, abbreviated PME). Strains with acquired resistance to colistin and/or carbapenems and/or broad spectrum cephalosporins were pre-selected and included in all organism groups evaluated.

MIC testing was performed according to Clinical and Laboratory Standards Institute (CLSI) M7-A7 (2006) broth microdilution methods. Unless otherwise indicated, MIC values are provided in units of micrograms per milliliter.

One day prior to testing, individual colonies were isolated by streaking onto rich, non-selective Tryptic Soy agar with 5% lysed sheeps blood (TSAB) with incubation at 35-37° C. for 18-24 hours.

Cultures were prepared by touching 3-5 colonies into 3 mL of Cation adjusted Mueller Hinton Broth (caMHB) in a 14 mL tube (CaMHB was prepared and sterilized according to manufacturer's specifications). Cultures were grown at 37° C. 200 rpm for approximately four hours prior to density adjustment for addition to the MIC assay.

$OD_{600}$ of growing cultures was measured and adjusted to approximately $10^5$ colony forming units per mL (CFU/mL) in caMHB for MIC inoculation (approximately $OD_{600}$ 0.001).

Diluted cultures were used to inoculate 50 μL per well in broth microdilution assays (final volume 100 μl per well; compounds were prepared in two-fold dilutions).

Plates were incubated 16-20 hrs at 37° C., with shaking at 200 rpm.

$OD_{600}$ was determined for all wells. Growth was defined as $OD_{600}$>0.1. MICs were defined as the lowest concentration producing no visible turbidity ($OD_{600}$<0.1).

TABLE 3A $MIC_{90}$ for Compounds of Formula (I) (Compounds 5 and 6) (micrograms/mL)

| Species | # strains | Compound 6 | Compound 5 | PMB | PME |
|---|---|---|---|---|---|
| P. aeruginosa | 100 | 8 | 2 | 2 | 2 |
| Acinetobacter spp | 81 | 2 | 4 | 2 | 4 |

TABLE 3A-continued

MIC$_{90}$ for Compounds of Formula (I) (Compounds 5 and 6) (micrograms/mL)

| Species | # strains | Compound 6 | Compound 5 | PMB | PME |
|---|---|---|---|---|---|
| S. maltophilia | 25 | 16 | >16 | 8 | 16 |
| E. coli | 80 | 4 | 2 | 2 | 2* |
| K. pneumonia | 81 | 4 | 4 | 2 | 4* |
| Citrobacter spp. | 20 | 1 | 0.5 | 1 | 0.5* |
| Enterobacter | 20 | >16 | >16 | >64 | >64* |

*some strains tested were multi-drug resistant

As shown by Table 3A, Compound 5 showed in vitro activity and spectrum similar to that of colistin (PME). It was active against colistin susceptible *P. aeruginosa* and *Acinetobacter* spp., including multi-drug resistant strains. Compound 5 was also active against *E. coli, K. pneumonia, Citrobacter* spp. and had some activity against *Enterobacter* spp. isolates. Compound 5 showed limited activity against organisms intrinsically resistant to colistin, such as indole-positive *Proteae, P. mirabilis*, and *S. marcescans*.

As shown by Table 3A (showing MIC$_{90}$ measurements for the indicated strains), Compound 6 also showed in vitro activity and spectrum similar to those of colistin (PME) and Compound 5. For example, Compound 6 was active against colistin susceptible *Acinetobacter* spp., including multi-drug resistant strains, and was also active against *E. coli, K. pneumonia, Citrobacter* spp. Compound 6 also had similar activity to compound 5 against *Enterobacter* spp. isolates. However, Compound 6 showed an approximately 4-fold decrease in activity against colistin susceptible *P. aeruginosa*, whereas Compound 5 exhibited similar activity to that of colistin. Thus, for at least this reason, Compound 5 shows surprising and unexpected properties, despite the similar structural resemblance to Compound 6.

TABLE 3B

MIC for Compounds of Formula (I) (Compounds 3 and 5) (micrograms/mL)

| Species | Compound 3 | Compound 5 |
|---|---|---|
| Acinetobacter baumannii 1570 | 8 | 4 |
| E. coli 1699 | 4 | 2 |
| P. aeruginosa 44 | 4 | 1 |
| K. pneumonia 21 | 4 | 2 |

As shown by Table 3B, Compound 5 showed superior in vitro antibacterial activity and spectrum compared to Compound 3. For example, Compound 5 was more active than Compound 3 against strains of *Acinetobacter baumannii, E. coli, P. aeruginosa*, and *K. pneumonia*. Compound 5 was selected for cell culture cytotoxicity based on superior antibacterial properties compared to Compound 3. The 4-chlorophenyl isomer (Compound 3) was less efficacious in comparison to both Compound 5 and polymyxin B.

Cell Culture Cytotoxicity Assay

Cell culture cytoxicity assays were performed on compounds of Formula (II) having in vitro antibacterial properties comparable or better than that of polymyxin B1 (PMB). Surprisingly, as shown in Table 4, the 3-chlorophenyl analog (Compound 4) exhibited higher toxicity (an EC$_{50}$ of 691) than the structurally similar 2-chlorophenyl analogue (Compound 5, an EC$_{50}$ of >1000), while both compounds exhibited antibacterial activity comparable to each other and to Polymyxin B (e.g., MIC values of 2 micrograms/mL in Table 4) against *P. aeruginosa*.

Day 1: $1 \times 10^5$ to $2 \times 10^5$ cells were inoculated (Cell line: LLC-PK1) per flask, containing 4 mL/T25 flask of medium DMEM-F12 (50/50) media supplemented with 10% FBS (Fetal Bovine Serum). The cells were then incubated at 37° C., 5% $CO_2$, 80% RH.

Day 4: The cell cultures were examined to determine 80% confluency. To trypsinize of the 80% confluent flasks, 4 mL of DMEM-F12-10% FBS media was prepared per flask. The media was aspirated from the flask and 5 mL of Versene was added to rinse the flask. The Versene was aspirated and 2 mL of triple Express solution (trypsin solution) was added. The cells were incubated for 5 min at room temperature and examined via microscopy for the rounding of the cells and their detachment. To speed up the reaction, the flask can be incubated at 37° C. for 3 minutes. 4 mL of media (DMEM-F12-10%FBS) was added to stop the reaction. Using a 5 mL pipette, the completed reaction was pipetted up and down to ensure that the cells were properly detached from the flask and from each others. The cell number was counted using a hemocytometer slide. 100 μL of cell suspension was transferred to a tube and 100 μL of Trypan Blue was added. Inoculum for 96 well is 10,000 cells per well. For one 96 well plate, 26.3 μL×110 well=2893 μL total. 2.9 mL of cell suspension was mixed with 8.1 mL of media DMEM-F12-10% FBS and 100 μL was distributed to each well using a multi-channel pipetter. The plate was then Incubated for 24 h at 37° C.

Day 5: DMEM-F12 (no FBS) medium was dispensed into tubes with the test article to achieve final concentrations of 1000 mg/mL, 500 mg/mL, 250 mg/mL and 125 mg/mL. The 96 well plate was taken off the incubator and media was removed from each well using multichannel pipetter. 80 μL of serially diluted compounds of Formula (I) was added to each well. Every set of concentration was done in triplicate. Media and positive controls were added to each plate and the plates were incubated for 24 hours at 37° C.

Day 6: The plates were taken from the incubator, the media was removed from each well, and 100 μL of fresh media DMEM-F12 (this is equivalent to a rinse and the media can be replaced with PBS) was added. The media is then removed and 80 μL of cell lysis solution is added. After 5 minutes, 80 μL of sterile filtered high quality water was added to each well. Using a white or black 96 well reaction plate, 80 μL of 25× diluted ATP mix reagent (Sigma Bioluminescent Somatic Cell Assay Kit [cat #FL-ASC]) was added into one column. 80 μL of diluted ATP standards (dilutions used: 250, 500, 1000, 2000 and 4000) was added and the plate was read immediately in the topcount with a 2 second read time. In another white or black 96 well reaction plate, 80 μL of 25× diluted ATP mix reagent (plate A) was added and 80 μL of lysis-water solution was transferred to each column of plate A. The plate was then read immediately in the topcount with a 2 second read time. This process was repeated for next consecutive plate and the EC$_{50}$ for certain compounds of Formula I were calculated and provided in Table 4.

TABLE 4

MIC and EC$_{50}$ data for certain compounds of Formula (II)

| Compound No. | R$_1$ | R$_2$ | R$_3$ | MIC P. aeruginosa (micrograms/ml) | EC$_{50}$ Rat kidney proximal tubule cells (micrograms/ml) |
|---|---|---|---|---|---|
| 1 | —C(O)NH-phenyl | —CH$_2$CH(CH$_3$)$_2$ | H | 1 | >1000 |
| 2 | —C(O)NH-phenyl | —CH(CH$_3$)CH$_2$CH$_3$ | H | 2 | >1000 |
| 3 | —C(O)NH-4-chlorophenyl | —CH$_2$CH(CH$_3$)$_2$ | H | 4 | |
| 4 | —C(O)NH-3-chlorophenyl | —CH$_2$CH(CH$_3$)$_2$ | H | 2 | 691 |
| 5 | —C(O)NH-2-chlorophenyl | —CH$_2$CH(CH$_3$)$_2$ | H | 2 | >1000 |
| 6 | —C(O)NH-2-chlorophenyl | —CH(CH$_3$)CH$_2$CH$_3$ | H | 1 | >1000 |
| 7 | —C(O)NH-2,6-dichlorophenyl | —CH$_2$CH(CH$_3$)$_2$ | H | 2 | >1000 |
| 8 | —C(O)NH-2,6-dichlorophenyl | —CH(CH$_3$)CH$_2$CH$_3$ | H | 2 | |
| 9 | —C(O)NH-4-bromophenyl | —CH$_2$CH(CH$_3$)$_2$ | H | 2 | 502 |
| 10 | —C(O)NH-4-fluorophenyl | —CH$_2$CH(CH$_3$)$_2$ | H | 2 | >1000 |
| 11 | —C(O)NH-pentafluorophenyl | —CH$_2$CH(CH$_3$)$_2$ | H | 2 | 738 |
| 12 | —C(O)NH-2-chlorobenzyl | —CH$_2$CH(CH$_3$)$_2$ | H | | |
| 13 | —C(O)NH-2-chlorobenzyl | —CH(CH$_3$)CH$_2$CH$_3$ | H | 2 | |
| 14 | —C(O)NH-2,4-dichlorobenzyl | —CH$_2$CH(CH$_3$)$_2$ | H | 1 | 269 |
| 15 | —C(O)NH-2,4-dichlorobenzyl | —CH(CH$_3$)CH$_2$CH$_3$ | H | 1 | 267 |
| 16 | —C(O)NH-2-chloro-4-nitrophenyl | —CH$_2$CH(CH$_3$)$_2$ | H | 4 | >1000 |
| 17 | —C(O)NH-2-chloro-4-nitrophenyl | —CH(CH$_3$)CH$_2$CH$_3$ | H | | |
| PMB | NA | —CH$_2$CH(CH$_3$)$_2$ | H | 2 | 318 |

As shown by Table 4, Compound 5 showed comparable efficacy to polymyxin B against P. aeruginosa. In addition, Compound 5 is substantially less toxic (EC$_{50}$ of greater than 1000 in rat kidney proximal tubule cells) when compared to polymyxin B, which has an EC$_{50}$ of 318. Compound 5 is believed to be unique despite its structrual resemblance to other halogenated or nitro phenyl derviatives.

Example 6

Pharmacological Studies

Compound 5 was tested for efficacy in 8 models (both mouse models and rat models) with 5 different Gram negative pathogens. Efficacy was demonstrated in 7 out of 8 of these models. In the one model where Compound 5 did not show efficacy, none of the polymyxin compounds produced efficacy either. In the remaining 7 models, Compound 5 showed comparable efficacy to both polymyxin B and colistin. Data from two representative animal models is shown below.
In Vivo Efficacy of Compound 5 Against Lung Infection in Mice
Infection was induced in normal immunocompetent or neutropenic mice by intranasal inoculation of P. aeruginosa #44. Compound 5, polymyxin B, colistin, imipenem or ciprofloxacin were administered subcutaneously at 1 and 6 hours post-infection. At 24 hours post-infection, mice were humanely euthanized and the lungs of the mice were removed, homogenized, serially diluted, and plated on agar, to quantitate the bacterial burden. Compound 5, polymyxin B, colistin, ciprofloxacin and imipenem were evaluated for their ability to decrease the bacterial burden from the lungs compared with water-treated control mice.

P. aeruginosa #44 or K. pneumoniae #21 were grown in cation adjusted Mueller Hinton Broth (caMHB) (catalog #B12322; Fisher Scientific, Pittsburgh, Pa.) at 37° C. MIC testing was performed according to Clinical and Laboratory Standards Institute [CLSI, formerly National Committee for Clinical Laboratory Standards (NCCLS), Wayne, Pa.] guidelines for broth microdilution.

All of the test compounds were dissolved in sterile water for administration by subcutaneous (sc) injection. To dissolve ciprofloxacin, 2N HCl was added to the solution in small amounts until all the powder dissolved completely. A series of dilutions of test compounds were prepared in water.

In the lung infection model using P. aeruginosa #44 as the infecting organism, CD-1 mice were made neutropenic by intraperitoneal (ip) administration with 150 mg/kg cyclophosphamide on day-4, followed by a second ip dose of 100 mg/kg cyclophosphamide on day-1. On day 0 a diluted, exponential-phase growing culture of P. aeruginosa #44 corresponding to $1 \times 10^5$ or $2.5 \times 10^8$ CFU respectively, in 0.1 mL of sterile saline, was inoculated by the intranasal route in mice. Just prior to inoculation, mice were anaesthetized with 60 mg/kg pentobarbital, ip. The actual concentration of bacteria in the inoculum was confirmed by determination of viable counts by dilution plating on tryptic soy agar plates. The number of CFU of bacteria was determined after an incubation of 16 h at 37° C.

Groups of five mice were used for each dose of the test compounds and the vehicle (water) control group. Each group received sc injections of test compounds or vehicle at 1 hour post-infection, and then at 6 hours post-infection for a total of 2 doses. In each study, there were three to five dose groups per test compound.

Eighteen hours after the last injection, the mice were euthanized by asphyxiation with $CO_2$. The lungs were removed aseptically, homogenized in 4 mL of sterile, distilled water and dilution plated on tryptic soy agar plates to quantify bacterial CFU. The number of CFU of bacteria in lungs was determined after an incubation of 16 hours at 37° C. (the CFU per milliliter of homogenate).

The results were expressed as the geometric mean $\log_{10}$ CFU/mL±the standard deviation. The limit of detection was 10 CFU per mL of lung homogenate. Lungs were considered sterile when no CFU were detected on the agar. The efficacy of the test compounds was assessed by comparing the number of $\log_{10}$ CFU/mL measured in the infected and treated mice with control animals treated with water. The efficacy of Compound 5 was also compared with the positive comparator antibiotics polymyxin B, colistin, ciprofloxacin and imipenem-cilastatin.

Dose response curves of test compounds were generated for each isolate. Regression lines were generated in Microsoft Excel and used to calculate the dose expected to produce a 3 $\log_{10}$ reduction in bacterial count as compared to water-treated group [$ED_{-3\ log\ 10}$ (mg/kg, sc, BID)].

MIC testing was performed according to CLSI (formerly NCCLS) guidelines for broth microdilution. MICs of the compounds against *P. aeruginosa* #44 are shown in Table 5.

TABLE 5

MIC of Certain Compounds Against *P. aeruginosa* #44

| Compound | MIC (micrograms/ml) against *P. aeruginosa* #44 |
|---|---|
| 5 | 1-2 |
| Colistin | 2-4 |
| Polymyxin B | 1-2 |
| Imipenem-Cilastatin | 1-2 |
| Ciprofloxacin | 0.25 |

Compound 5 resulted in reduction of bacterial counts of *P. aeruginosa* #44 in the lungs of infected mice as shown in Table 6.

TABLE 6

In vivo Efficacy of Compound 5 Against Lung Infections in Mice

| Mice/ Bacterial isolate | Total daily dosage of Compound 5 (mg/kg/day) | $\log_{10}$ reduction in CFU/mL of lung homogenate |
|---|---|---|
| Neutropenic mice/ *P. aeruginosa* #44 | 8 | 1.0 |
|  | 16 | 1.7 |
|  | 24 | 2.4 |
|  | 32 | 4.0 |
|  | 40 | 4.0 |

In these studies, the efficacy of Compound 5 compared favorably to that of polymyxin B, colistin, ciprofloxacin, or imipenem-cilastatin against *P. aeruginosa* #44 lung infections in mice (see Table 7).

TABLE 7

Efficacy of Compound 5 and Comparator Antibiotics versus *P. aeruginosa* #44 Lung Infection in Neutropenic Mice

| Drug | Dosage (mg/kg, BID)[a] | $\log_{10}$ CFU/mL lung homogenate ± SD | $ED_{-3log10}$ (mg/kg, BID) |
|---|---|---|---|
| Compound 5 | 4.0 | 5.49 ± 1.27 | 9.05[b] |
|  | 8.0 | 4.86 ± 1.18 |  |
|  | 12.0 | 4.13 ± 1.46 |  |
|  | 16.0 | 2.56 ± 0.34 |  |
|  | 20.0 | 2.51 ± 0.70 |  |
| Polymyxin B | 4.0 | 6.48 ± 1.59 | 12.97 |
|  | 8.0 | 5.73 ± 1.92 |  |
|  | 12.0 | 3.47 ± 1.16 |  |
|  | 16.0 | 2.88 ± 1.07 |  |
|  | 20.0 | 2.71 ± 1.09 |  |
| Imipenem-Cilastatin | 2.5 | 3.33 ± 0.21 | 2.34 |
| Water | water | 6.53 ± 0.35 | — |

[a]Doses were administered 1 and 6 hours post-infection. Lungs were harvested at 24 hours.
[b]The dose has been corrected for potency of this lot (#CG-01-002) = 711 µg/mg.
The actual concentration of bacteria in the infection inoculum was $1 \times 10^5$ CFU in 0.1 mL of sterile saline that was inoculated into each mouse.

In Vivo Efficacy of Compound 5 against Thigh Infection in Mice

Infections were induced in neutropenic mice by intramuscular inoculation of into the left thigh of each mouse. Compound 5, or a comparator drug, either polymyxin B, colistin or imipenem, were administered subcutaneously at 1 hour and 6 hours post-infection. Eighteen hours after the last treatment, mice were euthanized humanely; the infected thighs were removed, homogenized, serially diluted, and plated on agar. The bacterial burden was then quantitated by colony count. Compound 5, polymyxin B, colistin, and imipenem were evaluated for their ability to decrease the bacterial burden in the infected thighs compared with water-treated control mice.

*A. baumannii* #1570 were grown in cation adjusted Mueller Hinton Broth (caMHB) (catalog #B12322; Fisher Scientific, Pittsburgh, Pa.) at 37° C. MIC testing was performed according to Clinical and Laboratory Standards Institute [CLSI, formerly National Committee for Clinical Laboratory Standards (NCCLS), Wayne, Pa.] guidelines for broth microdilution.

All the test compounds were dissolved in sterile water for administration by subcutaneous (sc) injection. A series of dilutions of test compounds were prepared in sterile water.

Mice were made neutropenic by ip administration with 150 mg/kg cyclophosphamide on day-4, followed by a second ip dose of 100 mg/kg cyclophosphamide on day-1. A diluted exponential-phase growing culture of *A. baumannii* #1570 corresponding to $1 \times 10^7$ or $5 \times 10^4$ CFU respectively, in 0.2 mL of sterile saline, was injected into the left thigh of conscious mice on day 0. The actual concentration of bacteria in the inoculum was confirmed by determination of viable counts by dilution plating on tryptic soy agar plates. The number of CFU of bacteria was determined after an incubation of 16 hours at 37° C.

Groups of five mice were used for each dose of the test compounds and the vehicle. Each group received sc injections of test compounds or vehicle at 1 hour post-infection, and then at 6 hours post-infection for a total of 2 doses. In each study, there were three to five dose groups per test compound. Eighteen hours after the last injection, the mice were euthanized by asphyxiation with $CO_2$. The left thighs were removed aseptically, homogenized in 4 mL of distilled water and dilution plated on tryptic soy agar plates to quantify bacterial CFU. The number of CFU of bacteria in thighs was determined after an incubation of 16 hours at 37° C. (the CFU per milliliter of homogenate).

The results were expressed as the geometric mean $\log_{10}$ CFU/mL±the standard deviation. The limit of detection was 10 CFU per mL of thigh homogenate. Thighs were considered sterile when no CFU were detected on the agar. The efficacy of the test compounds was assessed by comparing the number of $\log_{10}$ CFU/mL measured in the treated mice with control animals treated with vehicle (water). The efficacy of Compound 5 was also compared with the positive comparator antibiotics polymyxin B, colistin and imipenem-cilastatin.

Dose response curves of test compounds were generated for each isolate. Regression lines were generated using Microsoft Excel to calculate the dose administered twice daily (BID) predicted to produce a 3 $\log_{10}$ reduction in bacterial count as compared to the water-treated control group [$ED_{-3\,log\,10}$ (mg/kg, sc, BID)].

MIC testing was performed according to CLSI (formerly NCCLS) guidelines for broth microdilution. MIC of the compounds against *A. baumannii* #1570 is shown in Table 8.

TABLE 8

MIC of the compounds against *A. baumannii* #1570

| Compound | MIC (micrograms/ml) against *A. baumannii* #1570 |
|---|---|
| 5 | 2-4 |
| Colistin | 2 |
| Polymyxin B | 1-2 |
| Imipenem-Cilastatin | 1-2 |

Compound 5 produced a dose-dependent reduction of bacterial counts of the infected thigh muscles induced by *A. baumannii* #1570 as shown in Table 9.

TABLE 9

In vivo Efficacy of Compound 5 Against *A. baumannii* #1570 Thigh Infections in Neutropenic Mice

| Bacterial isolate (date of study) | Total Daily Dosage of Compound 5 (mg/kg/day) | Log10 reduction in CFU/mL of thigh homogenate |
|---|---|---|
| *A. baumannii* #1570 (Oct. 30, 2007) | 4.0 | 0.8 |
| | 8.0 | 1.1 |
| | 16.0 | 2.7 |
| | 24.0 | 3.8 |

In these studies, Compound 5 compared favorably to polymyxin B, colistin or imipenem-cilastatin against *A. baumannii* #1570 thigh infections in mice.

TABLE 10

Efficacy of Compound 5 and Comparator Antibiotics versus *A. baumannii* #1570 Thigh Infection in Neutropenic Mice: Study 2

| Drug | Dosage (mg/kg, BID)[a] | Log10 CFU/mL thigh homogenate ± SD | $ED_{-3log10}$ (mg/kg, BID) |
|---|---|---|---|
| Compound 5 | 2.0 | 6.93 ± 0.56 | 6.4[b] |
| | 4.0 | 6.64 ± 0.55 | |
| | 8.0 | 5.06 ± 0.80 | |
| | 12.0 | 3.97 ± 0.34 | |
| Polymyxin B | 2.0 | 6.04 ± 1.10 | 4.8 |
| | 4.0 | 4.94 ± 1.03 | |
| | 8.0 | 4.07 ± 0.41 | |
| | 12.0 | 4.19 ± 0.59 | |
| Imipenem-Cilastatin | 2.0 | 7.41 ± 0.15 | 9.6 |
| | 4.0 | 6.83 ± 0.52 | |
| | 8.0 | 4.99 ± 1.06 | |
| | 12.0 | 4.22 ± 0.40 | |
| Water | water | 7.75 ± 0.35 | — |

[a]Doses were administered 1 and 6 hours post-infection. Thighs were harvested at 24 hours.
[b]The dose has been corrected for potency of this lot (#CG-01-002) = 711 µg/mg.
The actual concentration of bacteria in the infection inoculum was $5.3 \times 10^6$ CFU in 0.2 mL of sterile saline that was injected into each mouse in this study performed on Oct. 30, 2007.

Example 7

Reduced Renal Toxicity of Compound 5 Compared to Polymyxin B

A comparative 7 day repeat dose safety study in cynomologous monkeys between polymyxin B and Compound 5 was performed.

Twenty five female, naïve cynomolgus monkeys were assigned to one of six dose groups as shown in the table below. Animals were 2.52 kg to 3.77 kg and were 4.2 to 5.7 years old. During acclimation, a chronic femoral intravenous catheter was implanted into all animals to permit continuous infusion. The femoral vein catheter was routed subcutaneously to exit through a prepared incision in the interscapular region. Animals were fitted with jackets connected to flexible stainless steel tethers that protected the catheters.

Monkeys were dosed twice or three times daily for seven days with control article (0.9% Sodium Chloride for Injection, USP), 25000 IU/kg Compound 5, 37500 IU/kg Compound 5, or 37500 IU/kg PMB (Alpharma, lot number A1411079). Each administration was given via a targeted 30-minute intravenous infusion. The study design for this experiment is shown in Table 11.

TABLE 11

Study Design for Safety Evaluation in Cynomologous Monkeys Between Polymyxin B and Compound 5

| Group | Test Article | Dose Frequency | Total Daily Dose Level (IU/kg) | Dose Level/ Administration (mg/kg) | Dose Level/ Administration (IU/kg) | Number of Animals (Female) |
|---|---|---|---|---|---|---|
| 1 | Control Article | TID | 0 | 0 | 0 | 5 |
| 2 | Compound 5 | BID | 75000 | 3.2 | 37500 | 5 |
| 3 | Compound 5 | TID | 75000 | 2.2 | 25000 | 4 |
| 4 | Compound 5 | TID | 112500 | 3.2 | 37500 | 3 |
| 5 | Polymyxin B | BID | 75000 | 3.8 | 37500 | 5 |
| 6 | Polymyxin B | TID | 112500 | 3.8 | 37500 | 3 |

The following parameters were evaluated: daily clinical observations and qualitative food consumption, body weight (twice prior to the first dosing and at necropsy), urinalysis, hematology, coagulation, serum chemistry, toxicokinetics, gross pathology, organ weights, and histopathology of the kidneys and injection sites, and of the liver and sciatic nerves of control and high dose groups. Animals were evaluated through Study Day 7 and then terminated.

In this comparative 7-day monkey study with the approved drug polymyxin B, notably less severe nephrotoxicity was observed with Compound 5 when the two drugs were compared at equivalent antibacterial activity doses (75,000 to 112,500 IU/kg), although higher $C_{max}$ and AUC values were apparent with polymyxin B.

Figure 2:
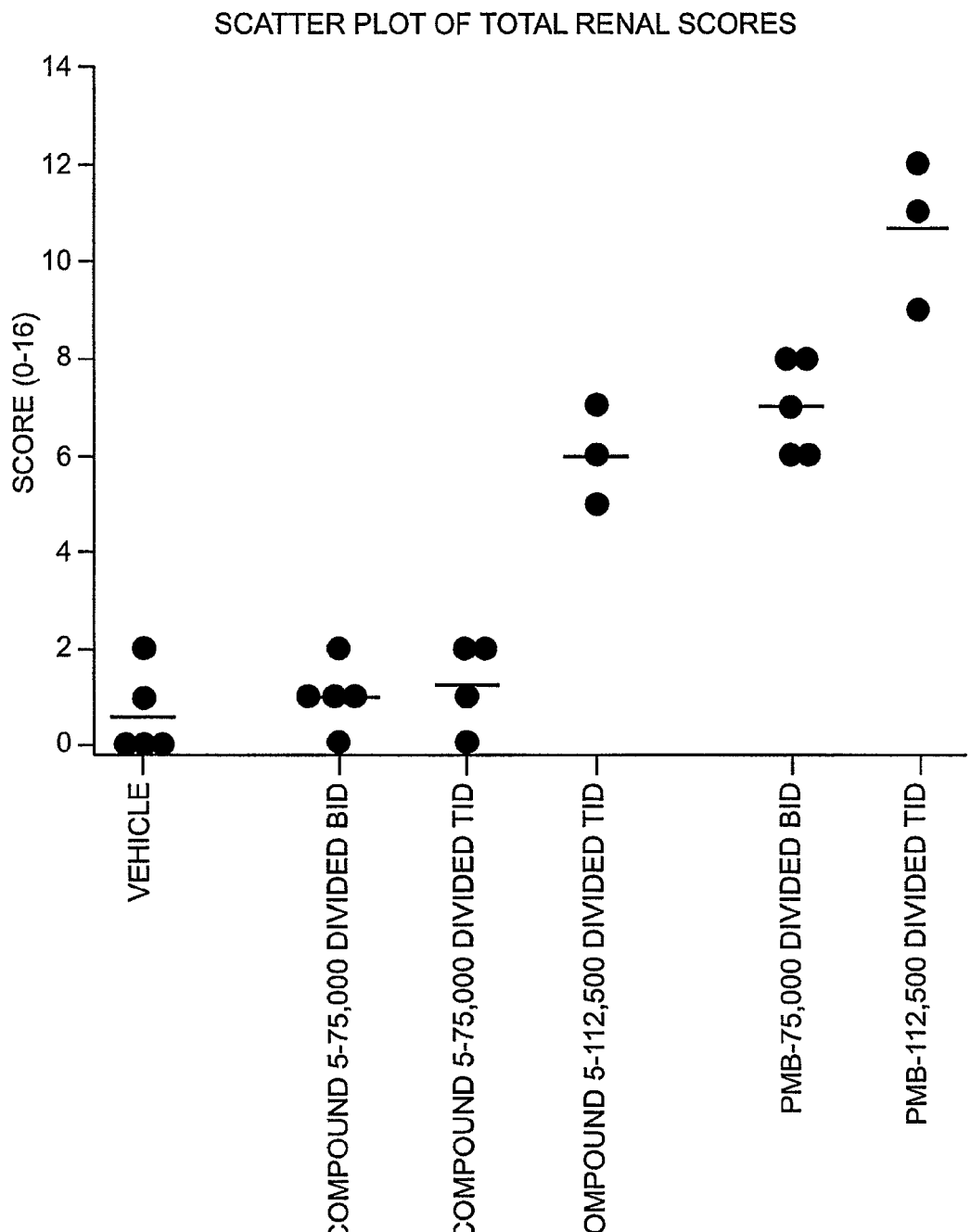
FIG. 2 is a scatter plot of total renal histopathology scores in monkeys.

The differences in nephrotoxicity between Compound 5 and polymyxin B are summarized in FIG. 2. FIG. 2 is a scatter plot showing nephrotoxicity data measured as a cumulative score based upon tubular degeneration, tubular regeneration, tubular dilatation, and tubular casts. Each category was scored on a basis from 0 to 4 based on the severity of each finding.

Primary test article-related changes occurred in the kidneys, and the severity of findings was lower for animals treated with Compound 5 than with an identical dose of polymyxin B. With Compound 5 findings were limited to very minimal histologic changes (minimal renal tubular degeneration, regeneration, casts or acute renal epithelial cell necrosis) in animals receiving 75,000 IU/kg/day. At the 112,500 IU/kg/day Compound 5 dose, histologic kidney changes consisted of increases in numbers and severity of cortical and medullary tubules containing necrotic or degenerative cells as compared to effects noted at the 75,000 IU/kg dose. In contrast, administration of 75,000 IU/kg/day of polymyxin B resulted in renal tubular histology similar to findings from animals receiving 112,500 IU/kg/day of Compound 5 (with an increase in the number of regenerative tubules observed). These findings were accompanied by mild increases in serum creatinine and BUN concentrations. In animals receiving 112,500 IU/kg/day of polymyxin B, the extent of histologic findings progressed to involvement of a majority of cortical and some medullary tubules containing necrotic or degenerate cells. These findings correlated with elevations in serum creatinine and blood urea nitrogen concentrations in animals given 112,500 IU/kg/day of polymyxin B.

For comparison of Compound 5 and polymyxin B, the nephrotoxicity was measured as a cumulative score based upon tubular degeneration, tubular regeneration, tubular dilatation, and tubular casts. Each category was scored on a basis from 0 to 4 based on the severity of each finding and individual monkeys are represented in the FIG. 2.

Compound 5 exhibited consistent and dose-dependent pharmacokinetic profiles in repeat-dose studies in cynomolgus monkeys, which was observed at clinically-relevant dose levels (i.e., ≦75,000 iu/kg in cynomolgus monkeys). At higher dose levels, a slightly greater than dose-proportional response was evident in systemic exposure (AUC) and peak plasma concentrations ($C_{max}$). The decrease in clearance at these higher doses may explain the non-linear systemic exposure to Compound 5. The clearance (CL) is less than hepatic blood flow, which suggests Compound 5 has minimal potential for hepatic extraction. The volume of distribution in all species was greater than blood volume, which suggests extravascular distribution of Compound 5.

The pharmacokinetic characteristics of Compound 5 as compared with those of polymyxin B, exhibited differences, most notably decreased serum protein binding, and increased plasma clearance and volume of distribution, which may lead to decreased potential for toxicity and potentially enhanced antibiotic efficacy through greater tissue distribution. Treatment with polymyxin B resulted in a systemic exposure (AUC) 2.5-fold greater than that observed with Compound 5 treatment at the same activity-normalized dose. Maximal plasma concentrations ($C_{max}$) of polymyxin B were approximately 2-fold greater than Compound 5 concentrations on Day 1, at the comparable activity dose of 37,500 IU/kg for both compounds. The higher systemic exposures evident at the same activity doses of polymyxin B could lead to greater potential for adverse effects (nephrotoxicity, and possible anaphylactoid reactions) as compared with Compound 5, at equally efficacious dose levels. Systemic clearance of polymyxin B on Day 1 was 2 to 3-fold less than that observed for Compound 5. Further, the volume of distribution observed following polymyxin B administration was approximately 2-fold lower than that observed following Compound 5 administration. The difference in volumes of distribution suggests that Compound 5 has an increased tissue distribution as compared with polymyxin B, which may lead to higher tissue levels (such as in the lung) for effective treatment of bacterial infection. The differences in clearance and volume of distribution between Compound 5 and polymyxin B may be related, partially, to the lower protein binding of Compound 5 (~30%) as compared to polymyxin B (~56%).

The kidney findings in female cynomolgus monkeys following seven days of repeated IV administration of Compound 5 were evident at dose levels of 6 mg/kg BID, 6 mg/kg QD, and 9 mg/kg QD, and to a lesser degree of severity at 3 and 4.5 mg/kg BID. Histopathological changes were characterized by minimal to mild degeneration/necrosis and regeneration of tubular epithelium, dilation of renal tubules, subacute interstitial inflammation, and cellular/granular and proteinaceous casts. There was an associated increase in blood urea nitrogen (BUN) and serum creatinine at dose levels of 6 mg/kg BID, 6 mg/kg QD, with 9 mg/kg QD exhibiting the most extensive kidney effects. The kidney findings in monkeys following seven days of repeated administration of Compound 5 by intravenous infusion were notably less than the marketed comparator polymyxin B when administered at equivalent antimicrobial doses.

Referring again to FIG. 2, Compound 5 was markedly less nephrotoxic as assessed micrscopically than polymyxin B (PMB) on a dose normalized basis. Primary test article-related changes occurred in the kidneys, and the severity of findings was lower for animals treated with Compound 5 than with an identical dosage of PMB. The profile of responses to administration of either Compound 5 or PMB were dose-dependent; minimal responses occurred in animals receiving 6.6 mg/kg/day, whereas responses were more extensive in animals receiving 9.9 mg/kg/day. Responses to Compound 5 were limited to very mild histologic changes (minimal renal tubular degeneration, regeneration, casts or acute renal epithelial cell necrosis) in animals receiving 6.6 mg/kg/day (about 3.3 mg/kg BID or about 2.2 mg/kg TID). Because the extent of the renal changes were limited and similar to background changes evident in the vehicle control animals, these effects were not considered to be adverse. At the 9.9 mg/kg/day (3.3 mg/kg TID) dose, histological kidney changes were increased in numbers and severity of cortical and medullary tubules containing necrotic or degenerative epithelial cells, regenerative tubules, casts, and mild interstitial lymphohistiocytic inflammation as compared to effects noted at the 6.6 mg/kg dose. In contrast, administration of 6.6 mg/kg/day of PMB resulted in renal tubular histology similar to findings from animals receiving 9.9 mg/kg/day of Compound 5 (with an increase in the number of regenerative tubules observed).

These findings were accompanied by mild increases in serum creatinine and blood urea nitrogen concentrations. In animals receiving 9.9 mg/kg/day of PMB, the extent of histologic findings progressed to involvement of a majority of cortical and some medullary tubules containing necrotic or degenerate epithelial cells, cast, and mild to moderate interstitial lymphohistiocytic and neutrophilic inflammation. These findings were correlated with the macroscopic observation of pale kidney in one animal as well as elevations in serum creatinine and blood urea nitrogen concentrations in animals given 9.9 mg/kg/day of PMB.

While some embodiments have been shown and described, various modifications and substitutions may be made thereto without departing from the spirit and scope of the invention. For example, it is not intended that the claims set forth hereinafter be construed narrower that the literal language thereof, nor is it intended that exemplary embodiments from the specification be read into the claims. Accordingly, it is to be understood that the present invention has been described herein by way of illustration only, and that such descriptions do not constitute limitations on the scope of the claims.

I claim:

1. A pharmaceutical composition comprising an antibacterial compound of the Formula:

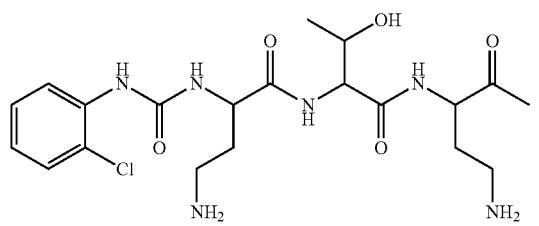

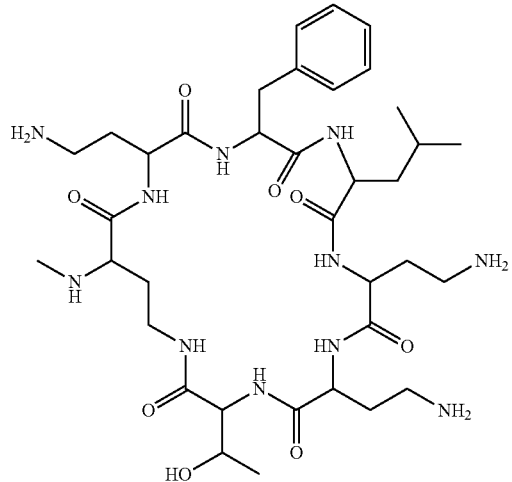

or a pharmaceutically acceptable salt thereof.

2. The composition of claim 1, further comprising a pharmaceutically acceptable carrier, wherein the antibacterial compound is (S)-4-amino-N-((2S,3R)-1-((S)-4-amino-1-oxo-1-((3S,6S,9S,12S,15R,18S,21S)-6,9,18-tris(2-aminoethyl)-15-benzyl-3-((R)-1-hydroxyethyl)-12-isobutyl-2,5,8,11,14,17,20-heptaoxo-1,4,7,10,13,16,19-heptaazacyclotricosan-21-ylamino)butan-2-ylamino)-3-hydroxy-1-oxobutan-2-yl)-2-(3-(2-chlorophenyl)ureido)butanamide.

3. The composition of claim 2, wherein the composition is adapted for intravenous administration.

4. The composition of claim 1, wherein the antibacterial compound has the Formula:

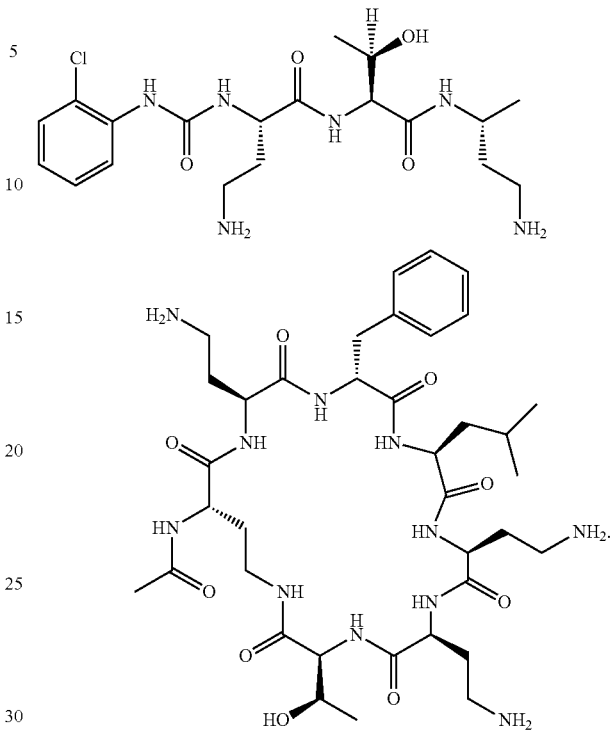

5. A method of treating a bacterial infection including a gram-negative bacteria, the method comprising administering to a subject in need thereof a therapeutically effective amount of a pharmaceutical composition comprising an antibacterial compound of the Formula:

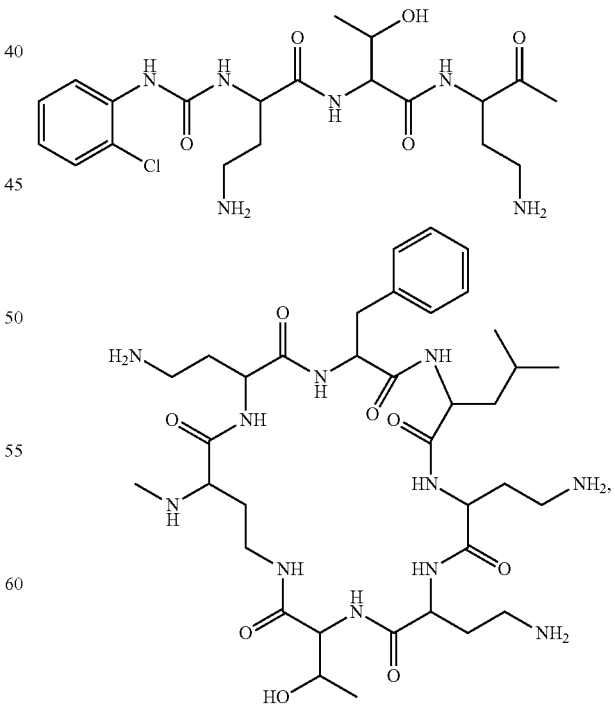

or a pharmaceutically acceptable salt thereof.

6. The method according to claim 5, wherein the subject is a human, an animal, a cell culture, or a plant.

7. The method according to claim 5, further comprising the step of determining the type of bacteria in the bacterial infection.

8. The method according to claim 7, wherein the type of bacteria in the bacterial infection includes a multi-drug resistant bacteria.

9. The method of claim 7, wherein the type of bacteria in the bacterial infection includes *Pseudomonas aeruginosa, Acinetobacter spp, Stenotrophomonas maltophilia, Escherichia coli, Klebsiella pneumoniae, Citrobacter spp, Enterobacter spp*, or a mixture comprising at least one of said bacteria.

10. The method of claim 5, wherein the antibacterial compound has the Formula:

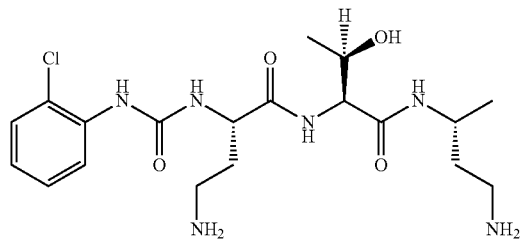

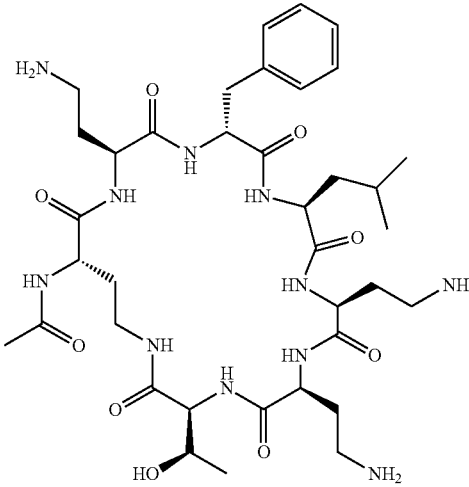

11. A process for preparing an antibacterial compound, the process comprising:
   (a) treating a polymyxin B with an amino protecting group comprising at least one acidic substituent to form a protected compound;
   (b) treating the protected compound with a deacylating agent, to form at least one deacylated protected compound;
   (c) treating the at least one deacylated protected compound with an isocyanate to form at least one acylated protected compound; and
   (d) treating the at least one acylated protected compound with an organic base to form the antibacterial compound having the Formula:

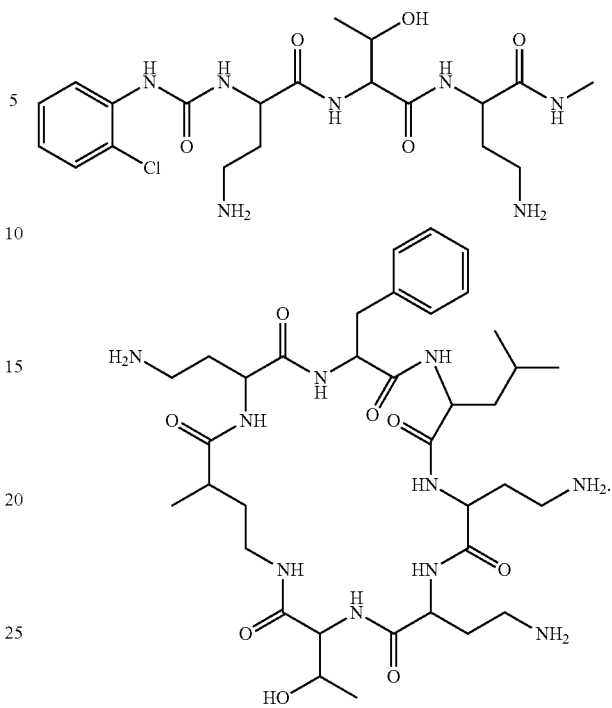

12. The process of claim 1, wherein the deacylating agent is produced by *Actinoplanes utahensis*; and the amino protecting group is 2-sulfo-9-fluorenylmethoxycarbonyl.

13. A compound of the Formula:

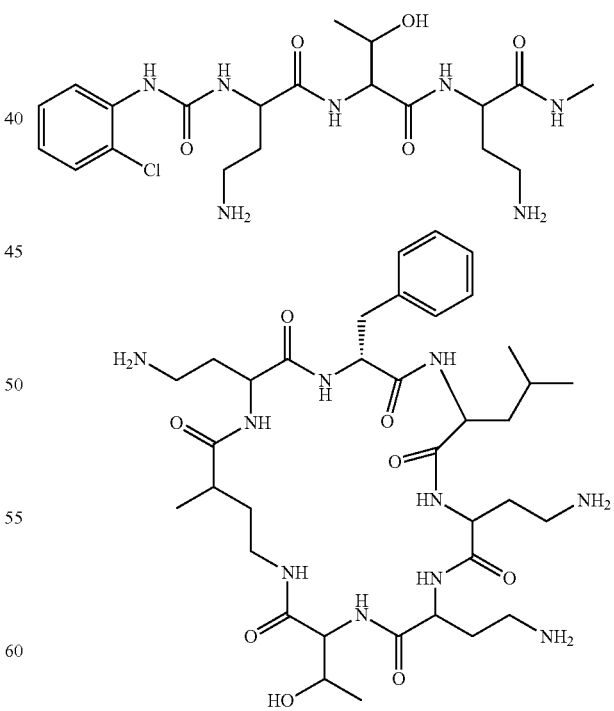

or a salt thereof.

14. The compound of claim 13, wherein the compound is (S)-4-amino-N-((2S,3R)-1-((S)-4-amino-1-oxo-1-((3S,6S,9S,12S,15R,18S,21S)-6,9,18-tris(2-aminoethyl)-15-benzyl-3-((R)-1-hydroxyethyl)-12-isobutyl-2,5,8,11,14,17,20-heptaoxo-1,4,7,10,13,16,19-heptaazacyclotricosan-21-ylamino)butan-2-ylamino)-3-hydroxy-1-oxobutan-2-yl)-2-(3-(2-chlorophenyl)ureido)butanamide, or salt thereof.

15. The method according to claim 7, wherein the type of bacteria in the bacterial infection includes a susceptible bacteria.

* * * * *

UNITED STATES PATENT AND TRADEMARK OFFICE
CERTIFICATE OF CORRECTION

PATENT NO.        : 8,343,912 B2
APPLICATION NO.   : 12/644943
DATED             : January 1, 2013
INVENTOR(S)       : Richard A. Leese Page 1 of 4

It is certified that error appears in the above-identified patent and that said Letters Patent is hereby corrected as shown below:

On the first page, in the Abstract section, please replace the existing formula with the following formula:

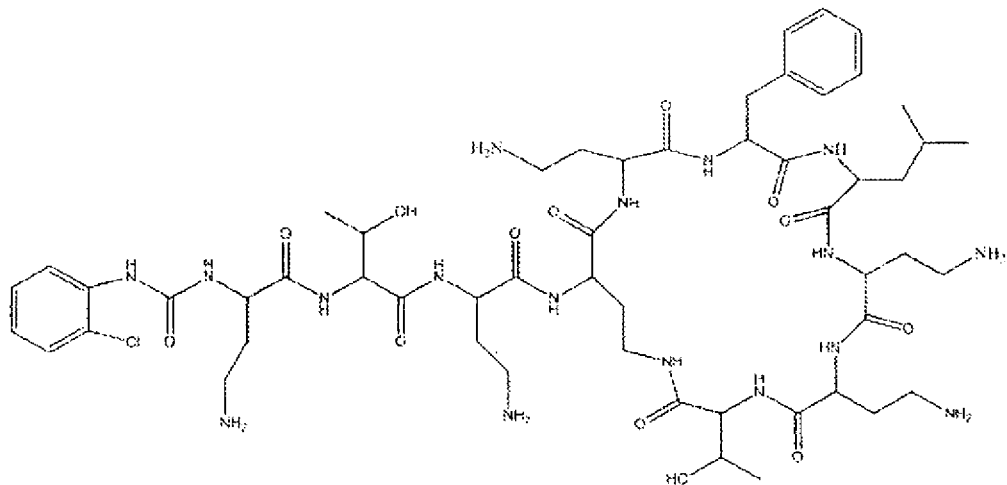

Signed and Sealed this
Seventh Day of May, 2013

Teresa Stanek Rea
*Acting Director of the United States Patent and Trademark Office*

CERTIFICATE OF CORRECTION (continued)
U.S. Pat. No. 8,343,912 B2

In the Claims:
In Column 41, lines 27-54, Claim 1, please replace the existing formula with the following formula:

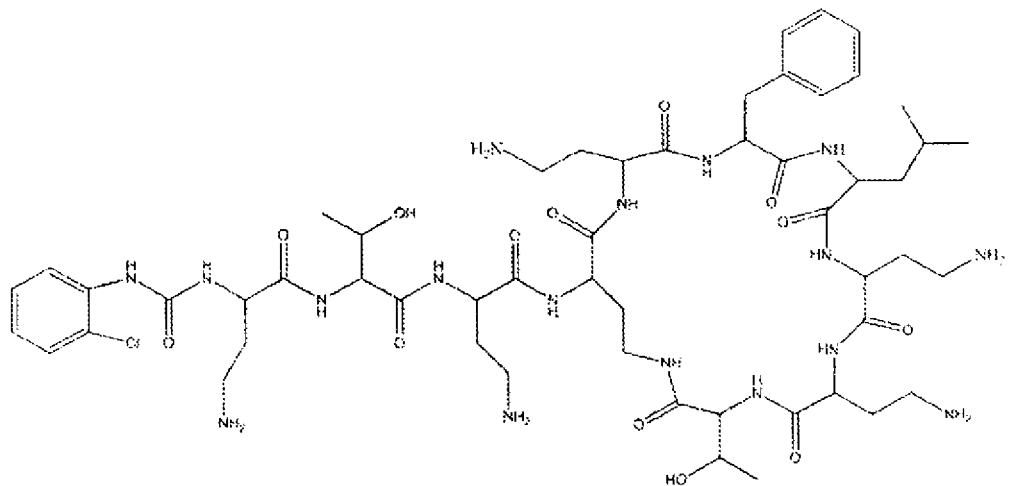

In Column 42, lines 3-32, Claim 4, please replace the existing formula with the following formula:

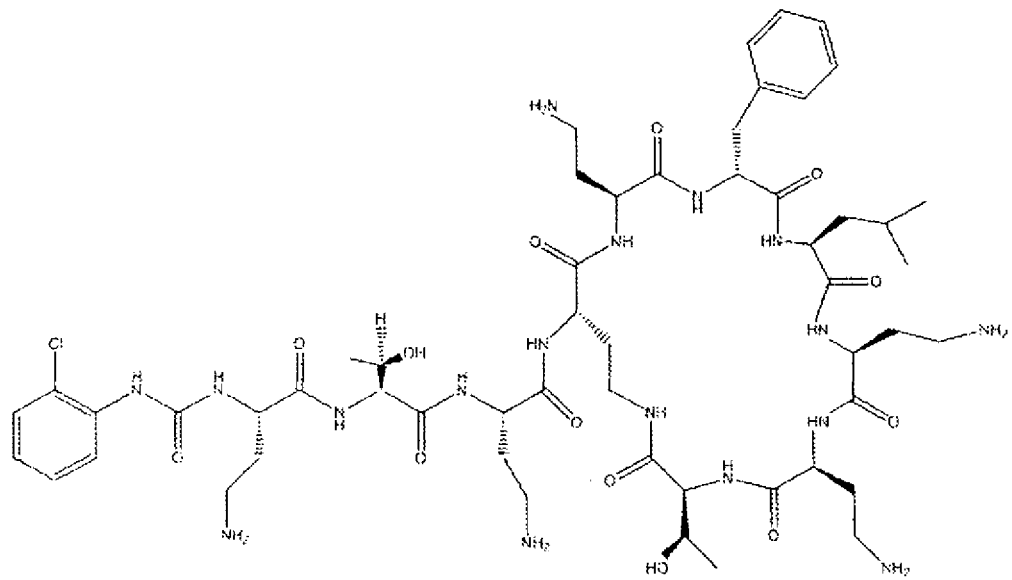

CERTIFICATE OF CORRECTION (continued)
U.S. Pat. No. 8,343,912 B2

In Column 42, lines 38-64, Claim 5, please replace the existing formula with the following formula:

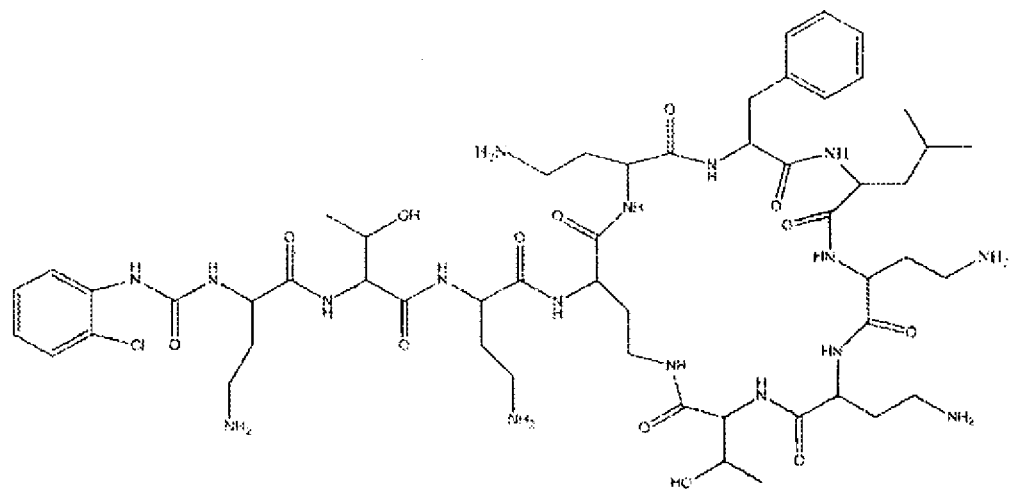

In Column 43, lines 19-48, Claim 10, please replace the existing formula with the following formula:

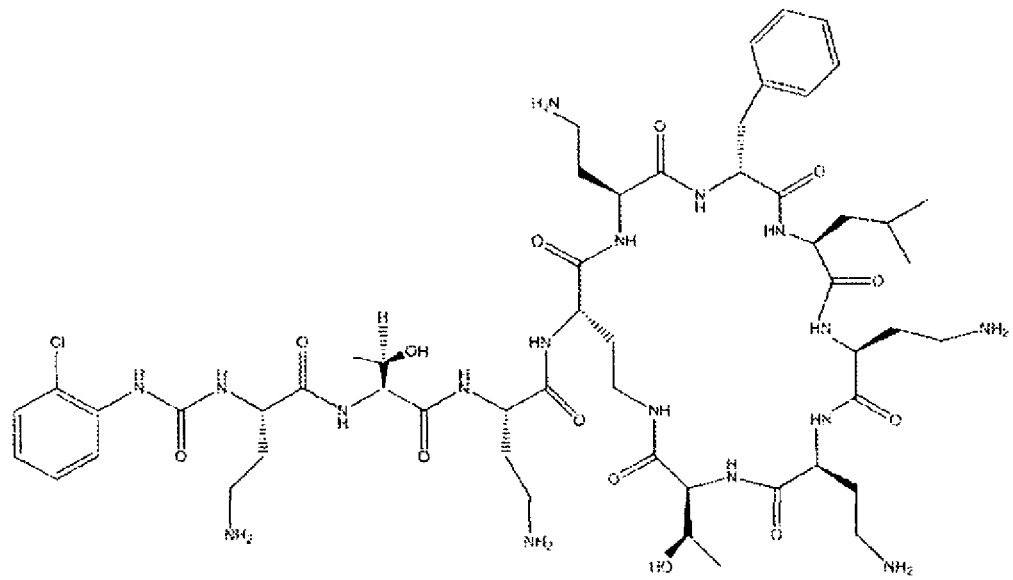

In Column 44, lines 1-28, Claim 11, please replace the existing formula with the following formula:
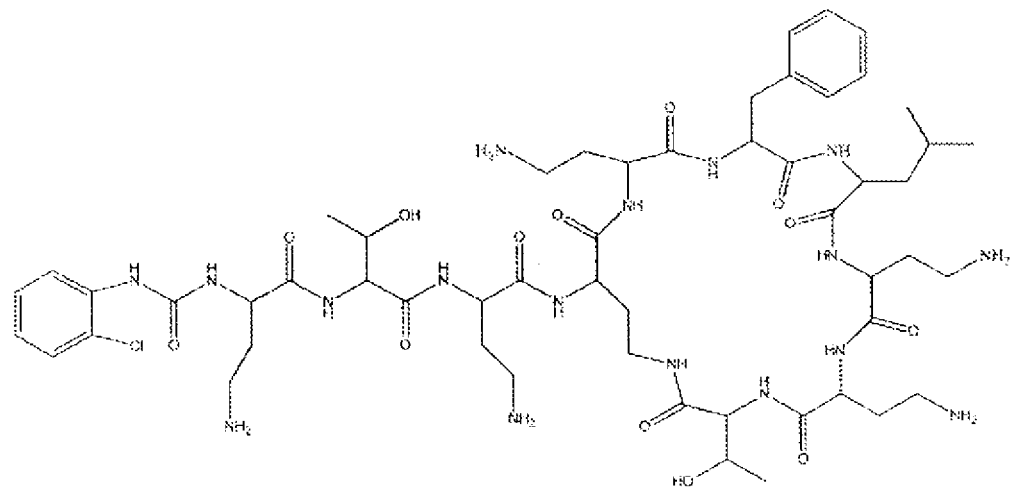
In Column 44, line 30, Claim 12, delete "claim 1" and insert --claim 11--.
In Column 44, lines 36-63, Claim 13, please replace the existing formula with the following formula:
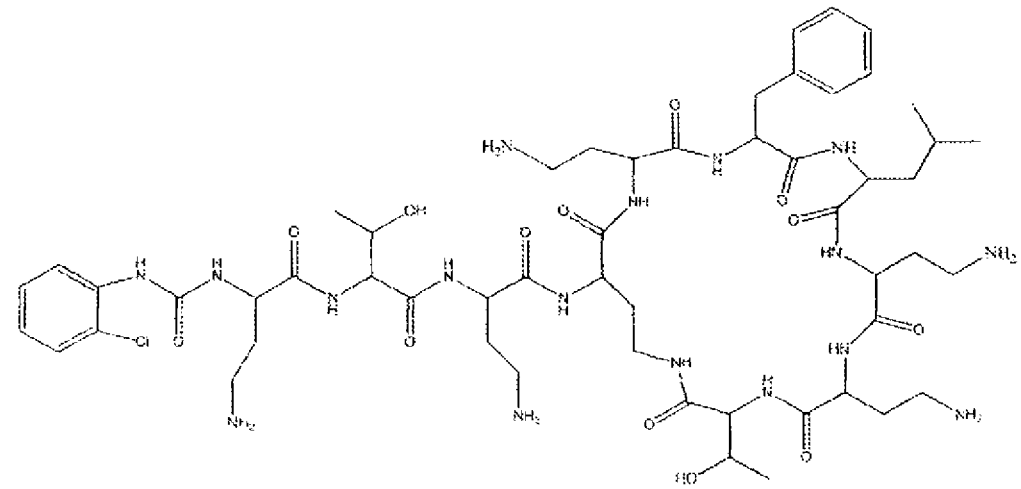
In Column 45, line 2, Claim 14, delete "N-( (2S,3R)" and insert --N-((2S,3R)--.